US012570970B2

(12) United States Patent
Becker et al.

(10) Patent No.: US 12,570,970 B2
(45) Date of Patent: Mar. 10, 2026

(54) INORGANIC PHOSPHATE AS A STABILIZER FOR PHYTASE ENZYMES

(71) Applicant: DANISCO US INC, Palo Alto, CA (US)

(72) Inventors: Nathaniel T. Becker, Palo Alto, CA (US); Mariliz Ortiz Johnson, San Mateo, CA (US); Amanda Jane Kalogrides, Palo Alto, CA (US); Michael J. Pepsin, Palo Alto, CA (US); Michael Reichman, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 1481 days.

(21) Appl. No.: 17/050,689

(22) PCT Filed: Apr. 18, 2019

(86) PCT No.: PCT/US2019/028117
§ 371 (c)(1),
(2) Date: Oct. 26, 2020

(87) PCT Pub. No.: WO2019/209623
PCT Pub. Date: Oct. 31, 2019

(65) Prior Publication Data
US 2021/0238578 A1      Aug. 5, 2021

Related U.S. Application Data

(60) Provisional application No. 62/662,802, filed on Apr. 26, 2018.

(51) Int. Cl.
*C12N 9/96* (2006.01)
*A23K 20/189* (2016.01)
*A23K 20/22* (2016.01)
*A23K 20/26* (2016.01)
*A23K 40/10* (2016.01)
*A23K 40/30* (2016.01)
*A23L 29/00* (2016.01)
*A23P 10/20* (2016.01)
*A23P 20/10* (2016.01)
*C12N 9/16* (2006.01)

(52) U.S. Cl.
CPC .............. *C12N 9/96* (2013.01); *A23K 20/189* (2016.05); *A23K 20/22* (2016.05); *A23K 20/26* (2016.05); *A23K 40/10* (2016.05); *A23K 40/30* (2016.05); *A23L 29/015* (2016.08); *A23L 29/06* (2016.08); *A23P 10/20* (2016.08); *A23P 20/10* (2016.08); *C12N 9/16* (2013.01); *A23V 2002/00* (2013.01)

(58) Field of Classification Search
CPC ...... A23K 20/189; A23K 20/22; A23K 40/30; A23K 40/25; A23K 40/10; A23K 20/26; A23P 20/10; A23P 10/20; A23L 29/06; A23L 29/015; A23L 29/05; A23V 2002/00
USPC .......................................................... 426/7
See application file for complete search history.

(56) References Cited

U.S. PATENT DOCUMENTS

2015/0037491 A1* 2/2015 Gebert ................... A23K 10/14
426/656

* cited by examiner

*Primary Examiner* — Subbalakshmi Prakash

(57) ABSTRACT

The present compositions and methods relate to thermostabilization of phytase with phosphate and increasing the recovery of phytase during the production of heat-treated food or animal feed pellets that contain phytase.

6 Claims, 11 Drawing Sheets

Specification includes a Sequence Listing.

INORGANIC PHOSPHATE AS A STABILIZER FOR PHYTASE ENZYMES

TECHNICAL FIELD

The present compositions and methods relate to thermo-stabilization of phytase with phosphate and increasing the recovery of phytase during the production of heat-treated food or animal feed pellets that contain phytase.

BACKGROUND

The use of active agents, such as enzymes, in foods and animal feed is common. Enzymes are known to improve digestibility of food or animal feed, reduce anti-nutritional factors in food and animal feed and improve animal pro-ductivity.

When compared with dry feed mixes, feed pellets have properties that are favored by the industry, such as improved feed quality, decreased pathogens, lower dust levels during manufacture, convenient handling, and more uniform ingre-dient dosing.

Preferred industry pelleting processes utilize steam injec-tion, in a process known as conditioning, which adds mois-ture and elevates the temperature prior to the pelleting step that forces the steam heated feed ingredients, or conditioned mash, through a die. The pelleting process temperatures are commonly from about 70° C. to 100° C. or higher.

Because of the steam, temperature, compression forces and chemicals used in pelleting processes, the activity or potency of enzymes are often significantly reduced during processing. The inactivation is at least partially reversible if the enzyme reactivates after processing and irreversible if the catalytic activity does not resume after processing. The irreversible inactivation of an enzyme is highly undesirable in processes such as pelleting.

There exists a need in the food and feed industries for stable, durable enzyme granules to serve as components in formulations that are subjected to steam pelleting processes without appreciable loss of enzyme activity.

SUMMARY

The present compositions and methods relate to increas-ing the stability of phytase in a composition using phos-phate, and recovery of phytase from animal feed pellets produced by steam pelletization.

1. In one aspect, a method for increasing the stability of a phytase in a solid composition, or the recovery of the phytase in a pelleting process comprising such solid composition is provided, the method comprising intro-ducing phosphate to the solid composition, wherein the phosphate and phytase are in functional proximity and at a molar ratio of at least 50:1, and wherein the solid composition comprises less than a 10:1 molar ratio of inositol or inositol phosphates to phytase.

2. In some embodiments of the method according to paragraph 1, the phytase and phosphate form, or are incorporated into or onto, a solid support.

3. In some embodiments of the method according to paragraph 1 or 2, the phytase and phosphate form, or are incorporated into, a granule.

4. In some embodiments of the method according to paragraph 3, the granule is a matrix granule.

5. In some embodiments of the method according to paragraph 3, the granule is a multi-layered granule.

6. In some embodiments of the method according to any of paragraph 5, the phytase and phosphate are incor-porated into a single layer of the multi-layered granule.

7. In some embodiments of the method according to any of paragraphs 3-6, the phytase and phosphate are incor-porated into the core of the granule.

8. In some embodiments of the method according to any of paragraphs 3-7, the granule is included in a food or animal feed pellet, wherein the percent recovered activ-ity following heat treatment is at least 75%, at least 80%, at least 85%, at least 90%, or at least 95%, or higher, following steam pelleting.

9. In some embodiments of the method according to any of paragraphs 3-8, the granule is included in a food or animal feed pellet, wherein the relative improvement in recovered activity is at least 10%, at least 20% at least 30%, at least 40%, or at least 50%, or more, after food or animal feed pelleting, compared to the recovered activity using, in the same a food or animal feed pellet, a granule that does not have phosphate and phytase in functional proximity and at a molar ratio of at least 50:1.

10. In another aspect, a method for increasing the stability of phytase in a liquid composition, or the recovery of the phytase in a pelleting process comprising such liquid composition is provided, the method comprising introducing phosphate to the composition, wherein the phosphate and phytase are in functional proximity and the phosphate is present at a concentration of 50 mM or more, and wherein the liquid composition comprises less than 10 mM inositol or inositol phosphates.

11. In some embodiments of the method according to paragraph 10, the phytase and phosphate are in solution or suspension.

12. In some embodiments of the method of paragraph 10 or 11, the phytase and phosphate are included in a food or animal feed pellet, wherein the percent recovered activity is at least 75%, at least 80%, at least 85%, at least 90%, or at least 95% after food or animal feed stem pelleting.

13. In some embodiments of the method of any of paragraphs 10-12, the phytase and phosphate are applied to the surface of a food or animal feed pellet, wherein the percent recovered activity is at least 75%, at least 80%, at least 85%, at least 90%, or at least 95% after food or animal feed stem pelleting.

14. In some embodiments of the method of any of paragraphs 10-13, the relative improvement in recov-ered activity is at least 10%, at least 20% at least 30%, at least 40%, or at least 50% after food or animal feed pelleting, compared to the recovered activity using, in the same a food or animal feed pellet, a granule that does not have phosphate and phytase in functional proximity with phosphate present at a concentration of 50 mM or more.

15. In some embodiments of the method of any of the preceding paragraphs, the phosphate is not a hydrolysis product of phytate present in the solid or liquid com-position.

16. In some embodiments of the method of any of the preceding paragraphs, the solid or liquid composition is essentially free of inositol or inositol phosphates.

17. In some embodiments of the method of any of the preceding paragraphs, the phosphate is a monophos-phate.

18. In some embodiments of the method of any the preceding paragraph paragraphs, the DSC Tm of the phytase is increased by at least 2.7° C. compared to a control phytase not stabilized by phosphate at a concentration molar ration of phosphate to phytase of at least 50:1 or a concentration of phosphate of at least 50 mM.

19. In another aspect, a granule composition comprising phosphate and phytase is provided, wherein the phosphate and phytase are in functional proximity and at a molar ration of at least 50:1 or phosphate is present in an amount of at least 50 mM phosphate.

20. In some embodiments of the granule according to paragraph 19, the granule is a matrix granule.

21. In some embodiments of the granule according to paragraph 19, the granule is a multi-layered granule.

22. In some embodiments of the granule according to paragraph 20, the phytase and phosphate are incorporated into a single layer of the multi-layered granule.

23. In some embodiments of the granule according to any of paragraphs 19-22, the phytase and phosphate are incorporated into the core of the granule.

24. In some embodiments of the granule according to any of paragraphs 19-22, the phosphate is not a hydrolysis product of phytate present in the solid or liquid composition.

25. In some embodiments of the granule according to any of paragraphs 19-22, the solid or liquid composition does not contain phytate.

26. In some embodiments of the granule according to any of paragraphs 19-22, the phosphate is a monophosphate.

27. In another aspect, a pellet composition comprising the granule of any of paragraphs 19-26 is provided.

28. In another aspect, a pellet composition comprising a phytase and phosphate in functional proximity and at a molar ration of at least 50:1 or wherein phosphate is present at a concentration of at least 50 mM is provided, wherein the phosphate is not a hydrolysis product of phytate present in the pellet composition.

These and other aspects and embodiments of present compositions and methods will be apparent from the description, including the accompanying Figures.

DETAILED DESCRIPTION

I. Definitions and Abbreviations

Figure 1:
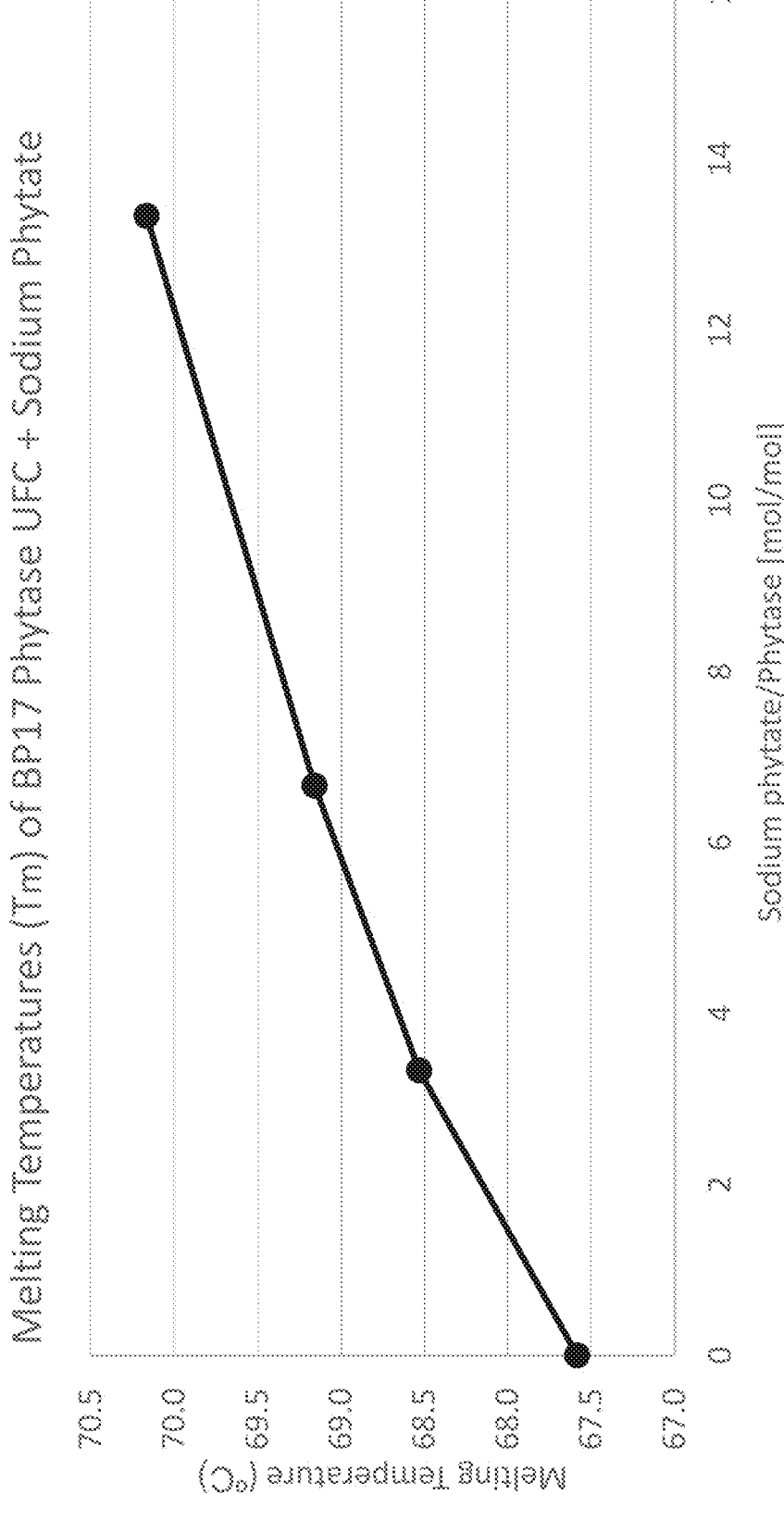
FIG. 1 is a graph showing the effect of adding increasing concentrations of sodium phytate to phytase on the melting temperature of the enzyme in the liquid state.

Prior to describing the present strains and methods in detail, the following terms are defined for clarity. Terms not defined should be accorded their ordinary meanings as used in the relevant art.

As used herein, the term "phytic acid" refers to inositol hexaphosphate (IP6), which may include minor amounts (i.e., less than 10%) inositol phosphates that are catabolites of IP6, including inositol pentaphosphate (IP5), inositol tetraphosphate (IP4), inositol triphosphate (IP3), inositol diphosphate (IP2), and inositol monophosphate (IP1), salts thereof, and mixtures thereof. The term "phytic acid" does not encompass inositol (IP0) or inorganic phosphate. Note that IP1, IP2, IP3, IP4, IP5 and IP6 are all referred to a "inositol phosphates."

As used herein, the term "phosphate" ($PO_4^{3-}$) refers to an inorganic chemical and a salt-forming anion of phosphoric acid. The term "phosphate" does not include IP6, IP5, IP4, IP3, IP2, IP1 or IP0.

As used herein, the term "food" is used in a broad sense—and covers food and food products for humans as well as food for non-human animals (i.e. a feed).

As used herein, the term "feed" is used with reference to products that are fed to animals in the rearing of livestock. The terms "feed" and "animal feed" are used interchangeably. The animals may be ruminants or non-ruminants. Examples of ruminants are cows, sheep, goats and horses. Examples of non-ruminant animals are mono-gastric animals such as pigs, poultry (such as chickens and turkeys), fish (such as salmon), dogs, cats, and humans.

As used herein, the term "food or feed ingredient" includes a formulation, which is or can be added to foods or foodstuffs and includes formulations that can be used at low levels in a wide variety of products. A food ingredient may be in the form of a solution or as a solid—depending on the use and/or the mode of application and/or the mode of administration. The enzymes described herein may be used as a food or feed ingredient or in the preparation or production. The enzymes may be, or may be added to, food supplements.

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) Nucleic Acids Res. 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF As used herein, the term "phytase" means a protein or polypeptide that is capable of catalysing the hydrolysis of esters of phosphoric acid, including phytate/phytic acid, and releasing inorganic phosphate.

As used herein, the terms "wild-type," "parental" or "reference," with respect to a polypeptide, refer to a naturally-occurring polypeptide that does not include a man-made substitution, insertion, or deletion at one or more amino acid positions. Similarly, the terms "wild-type," "parental" or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

As used herein, the term "variant," with respect to a polypeptide, refers to a polypeptide that differs from a specified wild-type, parental, or reference polypeptide in that it includes a man-made substitution, insertion, or deletion at one or more amino acid positions. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

As used herein, the terms "modification" and "alteration" are used interchangeably and mean to change or vary. In the context of modifying or altering a polypeptide, these terms may mean to change the amino acid sequence, either directly or by changing the encoding nucleic acid, or to change the structure of the polypeptide such as by glycosylating the enzyme.

As used herein, the term "solid support" refers to an inert solid material into or onto which the phytase and phosphate can be incorporated, e.g., by spraying, mixing, absorbing, or otherwise forming into particles such as granules or powders. Examples of solid supports include, but are not limited to, sodium sulfate, magnesium sulfate, granulated sucrose, starch-sucrose non-pareils (ASNP) and maltodextrin.

As used herein, the term "granule" refers to a small compact particle of a substance. The particle may be made from a matrix of materials or may include a core with one or more optional coating layers.

As used herein, the term "multi-layered granule" refers to a composition comprising a core and at least one coating layer.

As used herein, the term "matrix granule" refers to a granule having a homogenous structure including a matrix material and homogenously dispersed enzyme.

As used herein, the term "core" is interchangeable with the term "seed."

As used herein, the term "coating layer" and "layer" are interchangeable. The coating layer(s) generally encapsulates the core in order to form a substantially continuous layer so that the core surface has few or no uncoated areas. The materials (e.g., the agents, components and enzyme detailed herein) used in the granule and/or multi-layered granule are suitable for the use in foods and/or animal feeds. The materials can be food grade or feed grade.

As used herein, the term "outer coating layer" refers to the coating layer of the multi-layered granule that is the furthest from the core (i.e., the last coating layer that is applied).

As used herein, the term "enzyme coating layer" or "enzyme layer" refers to an enzyme layer that comprises at least one enzyme. In some embodiments the enzyme layer comprises at least two enzymes. In some embodiments, the enzyme layer comprises at least three enzymes.

As used herein, the term "functional proximity" means that the proximity of phosphate and phytase is such that the phosphate is capable of stabilizing the phytase. For example, phosphate and phytase are both in the same layer of a granule: for instance, phosphate and phytase are both in the core and/or phosphate and phytase are both in the same coating layer. In another example, phosphate and phytase are in adjacent coating layers of a granule. In a further example, phytase is in the core and phosphate is in the adjacent coating layer.

As used herein, the term "heat treatment" refers to steam pelleting or exposure to dry heat at a temperature above 90° C.

As used herein, the terms "pellets" and "pelleting" refer to solid, rounded, spherical and cylindrical tablets or pellets and the processes for forming such solid shapes, particularly feed pellets and solid, extruded animal feed. Known food and animal feed pelleting manufacturing processes generally include admixing together food or feed ingredients for about 1 to about 5 minutes at room temperature, transferring the resulting admixture to a surge bin, conveying the admixture to a steam conditioner, optionally transferring the steam conditioned admixture to an expander, transferring the admixture to the pellet mill or extruder, and finally transferring the pellets into a pellet cooler. Fairfield, D. 1994. Chapter 10, Pelleting Cost Center. In Feed Manufacturing Technology IV. (McEllhiney, ed.), American Feed Industry Association, Arlington, Va., pp. 110-139.

As used herein, the term "heat-treated food or animal feed pellets" refers to unpelleted admixtures that are subjected to a heat treatment (such as steam conditioning), typically at a temperature of at least 90° C. for at least 30 seconds. The admixture can then be extruded to form the animal feed pellets.

As used herein, the term "stability" refers to any of a variety of effects in which the enzymatic activity or other functional property of a phytase enzyme is beneficially maintained or improved. A phytase can exhibit stability by showing any of improved "recovered activity," "thermostability," and/or "inactivity reversibility." And "stability" can refer to activity maintained in phytase composition either prior to or after combination with feed or feed pellets.

As used herein, the term "recovered activity" refers to the amount of activity of a phytase after heat treatment compared to the amount of activity of the phytase before the heat treatment. The recovered activity may be expressed as a percentage. The percent recovered activity is calculated as follows:

$$\% \text{ recovered activity} = \left( \frac{\text{activity after treatment}}{\text{activity before treatment}} \right) \times 100\%$$

As used herein, the term "relative improvement in recovered activity" refers to the amount of recovered activity of stabilized phytase compared to the amount of recovered activity of unstabilized phytase. The recovered activity may be expressed as a percentage. Relative increase in recovery is calculated as follows:

$$\frac{\begin{array}{c}(\% \text{ recovered activity of stabilized phytase} - \\ \% \text{ recovered activity of unstabilized phytase})\end{array}}{\% \text{ recovered activity of unstabilized phytase}}$$

As used herein, an "FTU" or "phytase turnover unit" or "unit of phytase activity" or "Unit" is the amount of enzyme that is able generates 1 μmole of inorganic phosphorus per minute from an excess of sodium phytate at pH 5.5 and 37° C. Phytase activity is assayed according to Association of Analytical Chemists (AOAC) Official Method 2000.12, as described in "Determination of phytase activity in feed by a colorimetric enzymatic method: collaborative interlaboratory study" Engelen, A. J., van der Heeft, F. C., Randsdorp P. H., Somers, W. A., Schaefer. J., van der Vat, B. J. J AOAC Int. 2001 May-June: 84:629-33. Briefly, the ground samples are extracted in 220 mM sodium acetate trihydrate, 68.4 mM calcium chloride dehydrate, 0.01% Tween 20, pH 5.5. The supernatant is then assayed. The assay measures the release of inorganic phosphate from rice phytase, at pH 5.5, for 60 min at 37° C. The assay is stopped with acidic molybdate/vanadate reagent, and phosphate is quantified by intensity of yellow colored complex of the vanadomolybdophosphor.

As used herein, "melting temperature (Tm)" of the enzyme is the temperature at which 50% of the enzyme protein is in the unfolded non-native state, i.e. at which the free energy of the folded and unfolded states is equal, and can be measured by techniques known in the art. One suitable technique is differential scanning calorimetry (DSC). Other suitable techniques for determining melting temperatures include light scattering, circular dichroism and enzymology experiments.

For ease of reference, elements of the present compositions and methods may be arranged under one or more headings. It is to be noted that the compositions and methods under each of the headings also apply to the compositions and methods under the other headings.

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

° C. degrees Centigrade
g or gm gram
g/L grams per liter
g/mol grams per liter

8 mol/mol mole to mole ratio
HPLC high performance liquid chromatography
hr or h hour
kg kilogram
M molar
mg milligram
mL or ml milliliter
min minute
mM millimolar
cm centimeters
mm millimeters
nm nanometer
PCR polymerase chain reaction
rpm revolutions per minute
μg microgram
μL and μl microliter
μM micromolar
w/v weight/volume
FTU/g phytase units/gram
UFC ultrafiltrate concentrate
kW kilowatt
atm atmosphere
molar ratio mol:mol

II. Stabilization of Phytase Using Phosphate

The present compositions and methods are based on the surprising observation that the thermal stability of a phytase enzyme is increased following pre-incubation with a molar excess of inorganic phosphate relative to the phytase. Phosphate is an inexpensive formulation ingredient and can advantageously replace more expensive phytase-stabilizing excipients, such as phytate. Aspects and embodiments of the compositions and methods are described, below.

A. Sources of Phosphate

The phosphate used to stabilize phytase can be derived from an inorganic salt, such as a sodium, calcium, potassium, or aluminum salt, or from an organic compound. The source of phosphate is not critical to the present compositions and methods. Suitable phosphate salts include, at a minimum, monophosphates such as sodium phosphate (mono or dibasic), polyphosphates such as sodium hexametaphosphate and sodium trimetaphosphate, and pyrophosphates such as di-, tri- and tetrasodium diphosphate. It is likely that other phosphate forms would work, e.g., potassium, magnesium, calcium, iron, and ammonia salts of phosphoric acid, pyrophosphates, and others.

Phosphate used for stabilizing phytases according to the present compositions and methods is required to be added at significantly higher levels that what would typically or inherently be present in the ingredients of a food or animal feed that the phytase (such as in the form of a liquid, a powder, a matrix granule, or a multi-layered granule) with which phytate is admixed with before pelleting. In other words, the phosphate that is used for stabilizing phytase is an exogenous phosphate: the phosphate present in the ingredients of a food or animal feed is endogenous phosphate. The calculated amount of phosphate in the present compositions and methods does not include trace amounts of endogenous phosphate. The phosphate that is the subject of the present compositions and methods is exogenous phosphate placed in functional proximity to phytase for the intended purpose of stabilizing the phytase.

Furthermore, the phosphate that is used for stabilizing phytase according to the present compositions and methods is not derived from phytate or any hydrolysis product of phytate, including, for example, phytate or other inositol phosphates that was used to stabilize phytase. Phytate, IP5, IP4, IP3, IP2, or even IP0 (inositol) may additionally be added to a composition comprising phytase and phosphate but it is not the source of the phosphate. Alternatively, the present compositions may expressly not include phytate, IP5, IP4, IP3, IP2, and/or IP0, or may include only low levels of inositol or inositol phosphates, i.e. less than 10 mM or even less than 5 mM, or an inositol or inositol phosphate to phytase ration of less than 10:1 or even less than 5:1.

The amount of phosphate needed to stabilize phytase is a molar ratio of 50:1 compared to phytase or at a concentration of 50 mM or higher. This distinguishes the present composition and methods from those described by Gebert in (WO2013/119468), which required 10 millimolal phytate. Due to the much lower cost of phosphate compared to phytate (10-20-fold compared to phytate), and the fact that phosphate can be added at a lower mass percentage for a given amount of phytase, the present compositions and methods greatly reduce formulation costs. Phosphate is also available at a much higher purity that phytic acid, resulting in improved consistency of formulated products. Phosphate is widely availability as a bulk commodity, rather as a specialty chemical, and produces no end products, such as inositol or inositol phosphates.

In some embodiments, phytase is stabilized by at least 50 mM, at least 100 mM, at least 150 mM, at least 200 mM, at least 250 mM, at least 300 mM, at least 350 mM, at least 400 mM, at least 450 mM, at least 500 mM, at least 550 mM, or even at least 600 mM phosphate with respect to a liquid phytase composition (e.g., a UFC) prior to granulation.

In some embodiments, the molar ratio of phosphate to total phytase protein in functional proximity is at least 50:1, at least 100:1, at least 150:1, at least 200:1, at least 250:1, or even at least 300:1 referring to solid or liquid phytase compositions.

In some embodiments, the relative improvement in recovered activity of the phosphate-stabilized phytase is at least 10%, at least 20% at least 30%, at least 40%, at least 50%, or greater, as compared to otherwise identical phytase that is not stabilized by phosphate, as calculated using the % recovered activity formula provided herein.

Any means may be used to provide phosphate to the phytase, i.e., to place the phosphate and phytase in functional proximity. For example, a liquid comprising phosphate may be admixed with a liquid comprising phytase. In a further example, the phytase and phosphate are spray dried onto a solid support. In a particular embodiment, the phytase and phosphate are in functional proximity in a granule, for example a multi-layered granule or a matrix granule. The phosphate may be added in a salt form, e.g. as the mono- or di-basic salt of phosphoric acid, as phosphoric acid, or any combination of the above.

B. Suitable Phytases

A phytase is a protein or polypeptide that is capable of catalyzing the hydrolysis of esters of phosphoric acid, including those in inositol phosphates, such as phytate, thereby releasing inorganic phosphate. Some phytases are also capable of hydrolyzing at least some of the inositol-phosphates of intermediate degrees of phosphorylation, such as include IP5, IP4, IP3, IP2, IP1 or IP0. Phytase enzymes are added to foods and animal feeds to increase phosphate availability thus increasing the nutritional value of the product. The processing of the food or animal feed, for example under heat and high pressure, can denature the phytase and reduce its activity.

The phytase used in the present compositions and methods may be any phytase that is suitable for use in foods or animal feeds. In some embodiments, the enzyme is a 6-phytase (also called a 4-phytase" or phytate 6-phosphatase). In some embodiments, the enzyme is a histidine acid phytases (HAP), which is a group comprising members found among prokaryotes (e.g., appA phytase from *Escherichia coli*) and eukaryotes (phyA and B from *Aspergillus* sp., HAP phytases from yeast and plants. HAP phytases share a common active site motif at the N-terminal end and a motif at their C-terminal ends.

In one embodiment, the phytase is from *Escherichia coli, Citrobacter* braakii, *Peniophora lycii* or *Aspergillus niger*. In some embodiments, the phytase is from a Buttiauxella sp., for example, the phytase from Buttiauxella sp. strain P 1-29 deposited under accession number NCIMB 41248, or variants, thereof, such as BP-11, BP17 and BP-111.

The amino acid sequence of wild-type phytase from Buttiauxella sp. strain P 1-29 deposited under accession number NCIMB 41248 is shown, below as

```
SEQ ID NO: 1:
NDTPASGYQVEKVVILSRHGVRAPTKMTQTMRDVTPNTWPEWPVKLGYIT

PRGEHLISLMGGFYRQKFQQQGILSQGSCPTPNSIYVWADVDQRTLKTGE

AFLAGLAPQCGLTIHHQQNLEKADPLFHPVKAGTCSMDKTQVQQAVEKEA

QTPIDNLNQHYIPFLALMNTTLNFSTSAWCQKHSADKSCDLGLSMPSKLS

IKDNGNKVALDGAIGLSSTLAEIFLLEYAQGMPQAAWGNIHSEQEWASLL

KLHNVQFDLMARTPYIARHNGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ
```

The amino acid sequence of BP-11, a variant phytase of Buttiauxella sp. comprising 11 amino acid substitutions compared to the wild-type enzyme (SEQ ID NO: 1) is shown, below as

```
SEQ ID NO: 2:
NDTPASGYQVEKVVILSRHGVRAPTKMTQTMRDVTPNTWPEWPVKLGYIT

PRGEHLISLMGGFYRQKFQQQGILSQGSCPTPNSIYVWTDVDQRTLKTGE

AFLAGLAPQCGLTIHHQQNLEKADPLFHPVKAGICSMDKTQVQQAVEKEA

QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ
```

The amino acid sequence of BP-17, a variant phytase of a Buttiauxella sp. comprising 12 amino acid substitutions compared to the wild-type enzyme (SEQ ID NO: 1) is shown, below as

```
SEQ ID NO: 3:
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLEKADPLFHPVKAGICSMDKTQVQQAVEKEA
```

-continued

```
QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ
```

The amino acid sequence of BP-111, a variant phytase of Buttiauxella sp. comprising 21 amino acid substitutions compared to the wild-type (SEQ ID NO: 1) is shown, below as

```
SEQ ID NO: 4:
NDTPASGYQVEKVVILSRHGVRAPTKMTQTMRDVTPYTWPEWPVKLGYIT

PRGEHLISLMGGFYRQKFQQQGILPRGSCPTPNSIYVWTDVAQRTLKTGE

AFLAGLAPQCGLTIHHQQNLEKADPLFHPVKAGICSMDKTQVQQAVEKEA

QTPIDNLNQRYIPELALMNTILNFSKSPWCQKHSADKPCDLALSMPSKLS

IKDNGNEVSLDGAIGLSSTLAEIFLLEYAQGMPQVAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPPGSVQLKIPGCNDQTAEGYCPLSTFTR

VVSQSVEPGCQLQ
```

In some embodiment the phytase is one or more of QUANTUM®, QUANTUM® BLUE, PHYZYMEXP™, AXTRA® PHY, RONOZYME™ HIPHOS or NATUPHOS. Phytases are described in, e.g., WO2006038128, US2017143004, US2006141562, US2016362666, US2016289655, U.S. Pat. Nos. 9,365,840, 8,663,963, and US2015159149.

Phytases for use as described, herein, may be "precursor." "immature," or "full-length." in which case they include a signal sequence, or "mature," in which case they lack a signal sequence. Mature forms of the polypeptides are generally the most useful. Unless otherwise noted, the amino acid residue numbering used herein refers to the mature forms of the respective phytase polypeptides. The present amylase polypeptides may also be truncated to remove the N or C-termini, so long as the resulting polypeptides retain phytase activity.

Phytases are generally produced in microbial cells, e.g., bacterial or fungal cells. In some embodiments, the phytase is produced in a *Trichoderma* host cell. In some embodiments, the phytase is produced in a *Trichoderma* host cell that comprises a deletion of the endo-N-acetyl glucosaminidase gene (sometimes referred to as "endo-T"), which encodes an enzyme that removes N-linked glycosylation from proteins, including phytases. An exemplary endo-T delete strain is described in WO 09/114380.

The amount of phytase Units added to the food or animal feed will depend on the composition of the food or feed itself. Foods and feeds containing lower amounts of available phosphorous will generally require higher amounts of phytase activity. The amount of exogenous phytase required can be determined by the skilled person. In some embodiments, the amount of phytase incorporated into in a food or animal feed is between 0.1 to 20 Units phytase activity per gram of the food or animal feed. Typically, the amount of phytase is about 50 grams (12,000 U/g phytase granule) per metric ton (1,000 kg) of food or animal feed: this is equivalent to 0.6 units phytase per gram of food or animal feed.

In some embodiments, the phytase is in solution. In other embodiments, the phytase is in the solid state. In further embodiments, the phytase is spray dried onto a solid support or incorporated into a powder. In other embodiments, the phytase is incorporated into a granule such as a matrix granule or a multi-layered granule. In most embodiments, the phytase is ultimately incorporated into in a food or animal feed.

In some embodiments, phytase is present in a liquid or solid composition containing phosphate in an amount of at least 0.5% w/w, at least 1.0% w/w, at least 1.5% w/w, at least 2.0% w/w, at least 2.5% w/w, at least 3.0% w/w, at least 3.5% w/w, at least 4.0% w/w, at least 4.5% w/w, and even at least 5.0% w/w, or higher.

III. Compositions Comprising Phytase and Phosphate

Compositions comprising phytase and phosphate include liquid compositions as well as solid compositions, such as powder (including spray-dried powder) and granules (including solid granules and multi-layered granules). Examples of such compositions are to be described.

A. Liquid Food and Animal Feed Compositions

In some embodiments, the food or animal feed is a liquid such as a liquid feed. In other embodiments, the food or animal feed is a solid. As used herein, the term animal includes all animals, examples of which include non-ruminants (i.e., mono-gastric animals such as pigs and poultry, fish, dogs, cats, and humans) and ruminants (such as cows, sheep, goats and horses).

The food or animal feed may comprise vegetable proteins. Suitable sources of vegetable proteins are soy beans, soy bean meal, cereals (such as maize (corn), wheat, oats, barley, rye, and sorghum), cereal meals (such as corn meal, wheat meal, oat meal, barley meal, rye meal, sorghum meal, and canola meal), brans (such as what bran, and oat bran), oil seeds (such as rapeseed and sunflower seeds), oil seed meals (such as rapeseed meal), cottonseed meal, cabbage, beet and sugar beet.

The food or animal feed may comprise animal proteins. Suitable animal proteins include fish-meal and whey. The food or animal feed may comprise additives. Suitable additives include enzyme inhibitors, vitamins, trace minerals, macro minerals, coloring agents, aroma compounds, antimicrobial peptides (such as Leucocin A, Thanatin, and Tritrpticin), and enzymes.

The liquid phytase composition may be applied to solid animal feed composition, by either direct mixing into feed mash prior to palletization, or by post-pelleting liquid application (PPLA) of liquid phytase onto finished pellets.

B. Solid Food and Animal Feed Compositions

1. Types and Methods for Production

Solid supports and granules may be produced by a variety of fabrication techniques and from a variety of materials. Solid supports include inert solid material into or onto which the phytase and phytic acid are incorporated, e.g. by spraying, mixing, absorbing, or otherwise forming into particles such as granules or powders. Examples of solid supports include, but are not limited to, sodium sulfate, magnesium sulfate, granulated sucrose, starch-sucrose non-pareils (ASNP) and maltodextrin. The materials used in the core should be suitable for use in foods and/or animal feeds.

Granules may be made by, e.g., rotary atomization, wet granulation, dry granulation, spray drying, disc granulation, extrusion, pan coating, spheronization, drum granulation, fluid-bed agglomeration, high-shear granulation, fluid-bed spray coating, crystallization, precipitation, emulsion gelation, spinning disc atomization and other casting approaches, and prilling processes. See, e.g., U.S. Pat. Nos. 4,689,297 5,324,649, 454,332, 6,248,706, 6,534,466, EP656058B1 and EP804532B1 and U.S. Pat. No. The core of the granule may be the granule itself or the inner nucleus of a layered granule. The materials used in the core should be suitable for use in foods and/or animal feeds.

2. Particle Cores

The core may comprise one or more water soluble or dispersible agent(s), including but not limited to, sodium sulfate, sodium chloride, magnesium sulfate, zinc sulfate, and ammonium sulfate), citric acid, sugars (e.g., sucrose, lactose, glucose, granulated sucrose, maltodextrin and fructose), plasticizers (e.g., polyols, urea, dibutyl phthalate, and dimethyl phthalate), fibrous material (e.g., cellulose and cellulose derivatives such as hydroxyl-propyl-methyl cellulose, carboxy-methyl cellulose, and hydroxyl-ethyl cellulose), phosphate, and combinations thereof. Suitable dispersible agents include, but are not limited to, clays, nonpareils (combinations of sugar and starch: e.g., starch-sucrose non-pareils-ASNP), talc, silicates, carboxymethyl cellulose, starch, and combinations thereof.

In some embodiments, the core comprises mainly sodium sulfate. In some embodiments, the core consists essentially of sodium sulfate. In a particular embodiment, the core consists of only sodium sulfate.

In some embodiments, the core comprises both phytase and phosphate in functional proximity. In other embodiments, the core comprises one or more enzymes in addition to phytase. In other embodiments, the core comprises one or more enzymes other than phytase. In other embodiments, the core is inert and does not comprise enzymes.

In some embodiments, the core is an enzyme powder, including UFC containing an enzyme. The enzyme powder may be spray dried and may optionally be admixed with any of the water soluble or dispersible agents listed, herein. The enzyme may be, or may include, the phytase to be stabilized, in which case the enzyme power should further include phosphate.

3. Coating Layers

In some embodiments the core is coated with at least one coating layer. In a particular embodiment, the core is coated with at least two coating layers. In another particular embodiment the core is coated with at least three coating layers. The materials used in the coating layer(s) can be suitable for use in foods and/or animal feeds (see, e.g., US20100124586, WO9932595 and U.S. Pat. No. 5,324,649.

In some embodiments, a coating layer comprises one of more of the following materials: an inorganic salt (e.g., sodium sulfate, sodium chloride, magnesium sulfate, zinc sulfate, and ammonium sulfate), citric acid, a sugar (e.g., sucrose, lactose, glucose, and fructose), a plasticizer (e.g., polyols, urea, dibutyl phthalate, and dimethyl phthalate), fibrous material (e.g., cellulose and cellulose derivatives such as hydroxyl-propyl-methyl cellulose, carboxy-methyl cellulose, and hydroxyl-ethyl cellulose), clay, nonpareil (a combination of sugar and starch), silicate, carboxymethyl cellulose, phosphate, starch (e.g., corn starch), fats, oils (e.g., rapeseed oil, and paraffin oil), lipids, vinyl polymers, vinyl copolymers, polyvinyl alcohol (PVA), plasticizers (e.g., polyols, urea, dibutyl phthalate, dimethyl phthalate, and water), anti-agglomeration agents (e.g., talc, clays, amorphous silica, and titanium dioxide), anti-foam agents (such as FOAMBLAST 882® and EROL 6000K®), and talc. US20100124586. WO9932595, and U.S. Pat. No. 5,324,649 detail suitable components for the coating layers.

In some embodiments, the coating layer comprises sugars (e.g., sucrose, lactose, glucose, granulated sucrose, maltodextrin and fructose). In some embodiments, the coating layer comprises a polymer such as polyvinyl alcohol (PVA). Suitable PVA for incorporation in the coating layer(s) of the multi-layered granule include partially hydrolyzed, fully hydrolyzed and intermediately hydrolyzed having low to high degrees of viscosity. In some embodiments, the coating layer comprises an inorganic salt, such as sodium sulfate. In some embodiments, the coating layer comprises phosphate.

4. Enzyme Coating Layers

In some embodiments, at least one coating layer is an enzyme coating layer. In some embodiments the core is coated with at least two enzyme layers. In another embodiment the core is coated with at least three or more enzyme layers.

In some embodiments, the enzymes are phytase in combination with one or more additional enzymes selected from the group consisting of phytases, xylanases, phosphatases, amylases, esterases, redox enzymes, lipases, transferases, cellulases, hemi-cellulases, beta-glucanases, oxidases (e.g., hexose oxidases and maltose oxidoreductases), proteases and mixtures thereof. Generally, at least one enzyme coating layer comprises at least one phytase, and phosphate.

The above enzyme lists are examples only and are not meant to be exclusive. Any enzyme can be used in the granules described herein, including wild type, recombinant and variant enzymes of bacterial, fungal, yeast, plant, insect and animal sources, and acid, neutral or alkaline enzymes.

In some embodiments, the enzyme coating layer may further comprise one or more additional materials selected from the group consisting of: sugars (e.g., sucrose, lactose, glucose, granulated sucrose, maltodextrin and fructose), starch (e.g., corn starch), fats, oils (e.g., rapeseed oil, and paraffin oil), lipids, vinyl polymers, vinyl copolymers, polyvinyl alcohol (PVA), plasticizers (e.g., polyols, urea, dibutyl phthalate, dimethyl phthalate, and water), anti-agglomeration agents (e.g., talc, clays, amorphous silica, and titanium dioxide), anti-foam agents (such as FOAMBLAST 882® and EROL 6000K® available from Ouvrie PMC, Lesquin, France), and talc. US20100124586, WO9932595, and U.S. Pat. No. 5,324,649 detail suitable components for granules. FOAMBLAST 882® is a defoamer made with food grade ingredients and is available from Emerald Foam Control, LLC.

4. Location and Distribution of Phosphate in Granules

Where the granule is a coated, in some embodiments the core includes both phytase and phosphate. In some embodiments the coating includes both phytase and phosphate. In some embodiments the core includes phytase and the coating includes phosphate. In some embodiments the core includes phosphate and the coating includes phytase. In some embodiments, a single enzyme coating layer comprises both phosphate and phytase. In some embodiments, a multiple enzyme coating layers comprises both phosphate and phytase. In some embodiments, phosphate and phytase are in adjacent layers, and therefore in functional proximity.

C. Food and Animal Feed Pellets

Pellets may comprise granules and/or multi-layered granules as described herein according to any of a variety of known pelleting methods, examples of which are described further below. In some embodiments, the pellet comprises phytase, phosphate and at least one food or feed ingredient.

In some embodiments, the pellet comprises at least one food or feed ingredient and a granule comprising phosphate and phytase.

Pellets of the present compositions and methods can be produced by a method in which the temperature of a feed mixture is raised to a high level in order to kill bacteria. The temperature is often raised by steam treatment prior to pelleting, a process known as conditioning. Subsequently, the conditioned feed mixture can be passed through a die to produce pellets of a particular size. The feed mixture can be prepared by mixing granules and/or multi-layered granules described herein with food or animal feed as described herein.

Generally, the steam conditioner treats the admixture for about 20 to about 90 seconds, and up to several minutes, at about 85° C. to about 95° C. or higher. The amount of steam may vary in accordance with the amount of moisture and the initial temperature of the food or animal feed mix. About 4% to about 6% added steam has been reported in pelleting processes, and the amount is selected to produce less than about 18% moisture in the mash prior to pelleting, or up to about 28% moisture in mash intended for extrusion.

An optional expander process can occur for about 4 to about 10 seconds at a temperature range of about 100° C. to about 140° C. The pellet mill portion of the manufacturing process typically operates for about 3 to about 5 seconds at a temperature of about 85° C. to about 95° C.

Prior to pelleting, unpelleted mixtures (so-called premixes or precursors, base mixes, mash, and diluents for pellets) typically contain vitamins and trace minerals. Base mixes typically contain food and animal feed ingredients such as dicalcium phosphate, limestone, salt and a vitamin and mineral premix, but not grains and protein ingredients. Diluents include, but are not limited to, grains (for example wheat middlings and rice bran) and clays, such as phyllo-silicates (the magnesium silicate sepiolite, bentonite, kaolin, montmorillonite, hectorite, saponite, beidellite, attapulgite, and stevensite). Clays also function as carriers and fluidizing agent, or diluents, for food and animal feed premixes. Mash typically comprises a complete animal diet. For example, the mash comprises or consists of corn, soy bean meal, soy oil, salt, DL Methionine, limestone, dicalcium phosphate and vitamins and minerals. In one example, the mash consists of 61.10% corn, 31.43% soybean meal 48, 4% soy oil, 0.40% salt, 0.20% DL Methionine, 1.16% limestone, 1.46% dical-cium phosphate and 0.25% vitamins and minerals.

In one embodiment, a food or an animal feed is produced by admixing at least one food or feed ingredient (such as a mash) with a phytase and phosphate in solution, steam conditioning the resulting admixture followed by pelleting the admixture. A liquid phytase composition may be applied to solid animal feed composition, by either direct mixing into feed mash prior to palletization, or by post-pelleting liquid application (PPLA) of liquid phytase onto finished pellets.

In one embodiment, a food or an animal feed is produced by admixing at least one food or animal feed ingredient (such as a mash) with a phytase and phosphate in the solid state (such as in a granule such as a multi-layered granule), steam conditioning the resulting admixture followed by pelleting the admixture.

For example, an unpelleted mixture of corn meal and soy meal (such as 60% corn meal and 40% soy meal) can be admixed with multi-layered granules comprising phytase and phosphate and then subjected to steam conditioning at 90° C. for 30 seconds. The admixture is then extruded to form the animal feed pellets.

In some embodiments, the compositions of the present compositions and methods can reside in heat-treated food or animal feed pellets. Such heat-treated food or animal feed pellets can be subjected to a heat treatment (such as steam conditioning) at a temperature of at least 90° C. for at least 30 seconds (e.g., at least 30-60 seconds at 90° C.-100° C.). The admixture can then be extruded to form the animal feed pellets.

IV. Methods and Processes Using Phosphate to Stabilize Phytase

Methods of use for the present compositions are primarily related to the addition of phytase to food and animal feed product that must be heat treated, such as by steam pelleting. The stability of phytase may be significantly improved in the liquid state and/or in the solid state compared to phytase that has not been stabilized by the use of phosphate. The present methods are an improvement on those described by Gebert in WO2013/119468, which required at least 10 millimolal phytate. Although the amount of phosphate needed to sta-bilize pytase is greater than the amount of phtate required, the much lower cost of phosphate compared to phytate greatly benefits formulation costs.

In some embodiments, phytase is stabilized by at least 50 mM, at least 100 mM, at least 150 mM, at least 200 mM, at least 250 mM, at least 300 mM, at least 350 mM, at least 400 mM. at least 450 mM, at least 500 mM, at least 550 mM, or even at least 600 mM phosphate with respect to a liquid phytase composition (e.g., a UFC) prior to granulation.

In some embodiments, the molar ratio (i.e., mol: mol) of phosphate to total phytase protein in functional proximity is at least 50:1, at least 100:1, at least 150:1, at least 200:1, at least 250:1, or even at least 300:1 referring to solid or liquid phytase compositions.

In some embodiments, phytase is present in a liquid composition containing phosphate in an amount of at least 0.5% w/w, at least 1.0% w/w, at least 1.5% w/w, at least 2.0% w/w, at least 2.5% w/w, at least 3.0% w/w, at least 3.5% w/w, at least 4.0% w/w, at least 4.5% w/w, and even at least 5.0% w/w.

In some embodiments, the recovered activity of the phos-phate-stabilized phytase is at least 5%, at least 10%, at least 15% at least 20%, at least 30%, or higher following heat treatment as compared to otherwise identical phytase that is not stabilized by phosphate, as calculated using the % recovered activity formula provided herein.

In some embodiments, the relative improvement in recov-ered activity of the phosphate-stabilized phytase is at least 10%, at least 20% at least 30%, at least 40%, at least 50%, or greater, as compared to otherwise identical phytase that is not stabilized by phosphate, as calculated using the % recovered activity formula provided herein.

VI. Combinations of Various Embodiments

Embodiments of the compositions and methods that are described, herein, including those described under different section headings, and other embodiments that would be apparent to the skilled person, can be combined unless the combination would defeat the asserted purposes and advan-tages of the present compositions and methods.

EXAMPLES

The following examples are intended to illustrate embodi-ments of the present compositions and methods and should not be construed in any way as limiting.

Example 1. Determination of Phytase Melting
Temperature in the Presence of Excipients An experiment was performed to determine whether the
addition of different excipients during thermal exposure
increases the melting temperature of the phytase enzyme in
the liquid state. Excipient solutions were prepared at their
highest solubility, then titrated from highest to lowest con-
centrations prior to their addition to the phytase UFC. The
enzyme/excipient combinations were then exposed to a
temperature profile of 21-95° C., and the melting tempera-
tures were measured via differential scanning fluorimetry.

Materials

The following equipment and reagents were used:

BP-17 phytase UFC (70,000 FTU/g or 123.4 g/L phytase)

Sodium phosphate, dibasic, anhydrous (J. T. Baker, Lot
V31149, FW 141.96)

Concentrated phosphoric acid for pH adjustment

Phytic acid sodium salt hydrate (Sigma Aldrich. P8810-
500G)

Sodium citrate dihydrate (J. T. Baker, FW 294.1)

Concentrated citric acid for pH adjustment

Sodium sulfate, anhydrous powder (FW 142.04)

Sulfuric acid for pH adjustment

Sodium polyphosphates, glassy (Spectrum, S0169,
60-71% $P_2O_5$)

10% NaOH for pH adjustment pH meter

Whatman Autovial syringeless filters, 0.45 μM

Prometheus NT.48 nanoDSF with Standard Capillaries
(NanoTemper Technologies)

Corning 3641 96-well clear flat bottom polytyrene non-
binding-surface microplates Corning 15 mL centrifuge tubes, polypropylene (Sigma
Aldrich)

Preparation of UFC

The concentration of phytase in the UFC was measured at
123.9 g/L via HPLC. The pH of the UFC was adjusted from
5.03 to 5.49 by adding 22 μL of 10% NaOH to 5 mL of the
UFC, diluting the phytase concentration to 123.36 g/L.

Preparation of Stabilizers

A 20% phytic acid solution was prepared by dissolving 1
gram of phytic acid into 5 mL of 0.1 M acetate buffer pH 5.5.
The pH was adjusted from 4.2 to 5.47 using 20% NaOH, and
then the solution was filtered using a 0.45 μM syringeless
filter. A 25% sodium sulfate anhydrous solution was pre-
pared by dissolving 5 grams into 20 mL of water. The pH
was adjusted to 5.6 using sulfuric acid, and then the solution
was filtered using a 0.45 μM syringeless filter. A 20%
sodium polyphosphate solution was prepared by dissolving
5 grams into 25 mL of water. The pH was adjusted to 5.6
using concentrated phosphoric acid, and then the solution
was filtered using a 0.45 M syringeless filter. A 25% sodium
citrate solution was prepared by dissolving 5 grams into 20
ml of water. The pH was adjusted to 5.6 using 80% citric
acid, and then the solution was filtered using a 0.45 μM
syringeless filter. A 20% sodium phosphate dibasic solution
was prepared by dissolving 2 grams into 10 mL of water. The
pH was adjusted to 5.6 using concentrated phosphoric acid,
and then the solution was filtered using a 0.45 μM syringe-
less filter.

Plate Setup for Excipient Dilutions

A volume of 100 μL of an excipient stock solution was
added to well A in column 1 of a 96-well plate. A volume of
50 μL of water was added to each well B-H in column 1 of
the same 96-well plate. The excipient stock solution was
titrated 2-fold down the column of the plate by transferring 50 μL into each subsequent well. A volume of 80 μL of the
pH adjusted UFC was added to each of the wells in column
1 of a new 96-well plate. A volume of 20 μL was transferred
from each well of the titrated excipient directly into the
corresponding well containing the UFC.

Differential Scanning Fluorimetry Setup

The 96-well plate containing the enzyme and excipient
combinations was mixed on a plate shaker for 5 seconds.
Standard capillaries for the nanoDSF were filled by dipping
a capillary in each well of the 96-well plate, and then loading
onto the Nanotemper instrument. The Nanotemper instru-
ment was programmed to run at 10% excitation power and
21-95° C. with a 1° C./minute ramp. The Nanotemper
instrument monitors the shift of intrinsic tryptophan fluo-
rescence of proteins upon unfolding by measuring wave-
lengths at 330 and 350 nm. The protein melting point (Tm)
is determined by analyzing the change in the ratio of the
fluorescence intensities (F350/F330) and is the maximum of
the derivative of the fluorescence vs. temperature curve.

Figure 2:
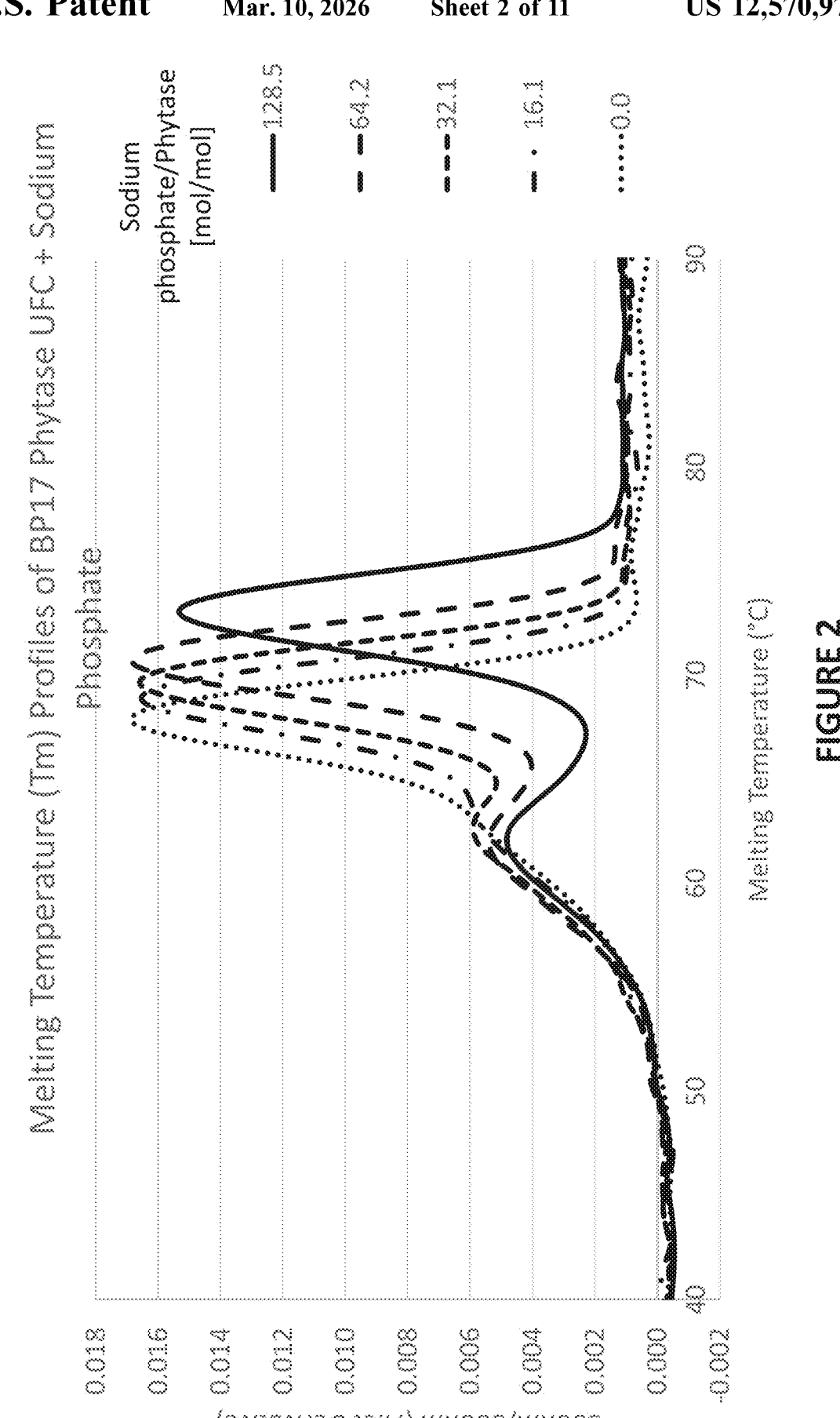
FIG. 2 is a graph showing the melting temperature profile of phytase UFC with increasing concentrations of sodium phosphate.
Figure 3:
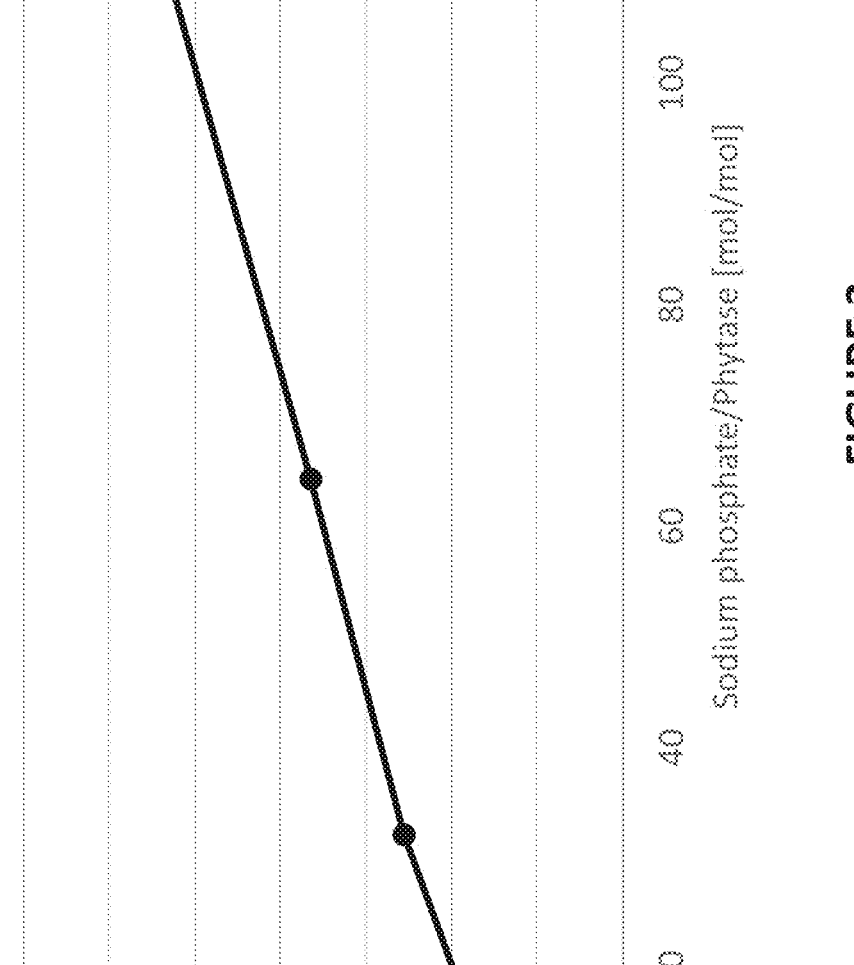
FIG. 3 is a graph showing the effect of adding increasing concentrations of sodium phosphate to phytase on the melting temperature of the enzyme in the liquid state.
Figure 4:
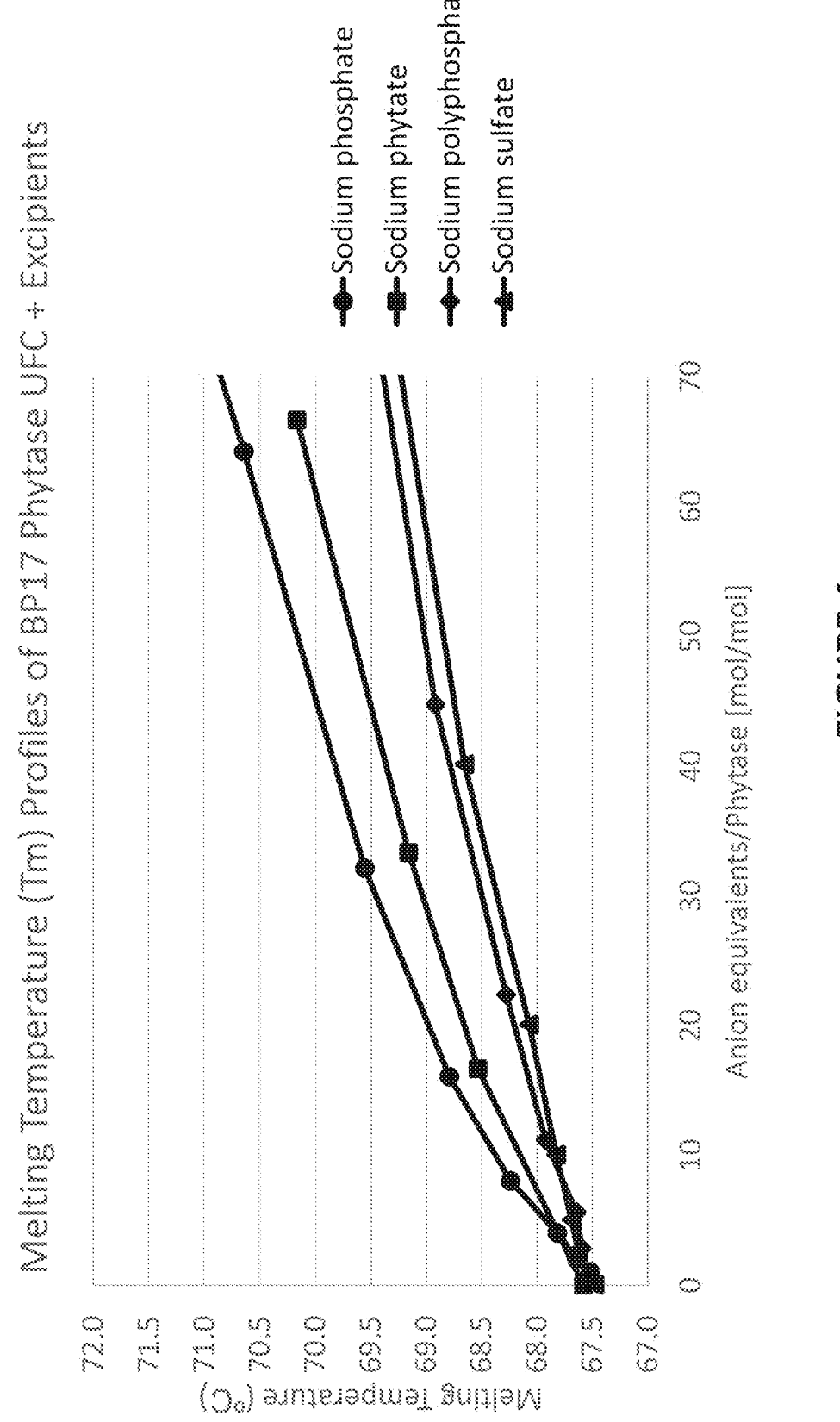
FIG. 4 is a graph showing a comparison of different excipients, normalized in anion equivalents, on the melting temperature of phytase in the liquid state.

As shown in FIG. 1, the Tm of phytase increased by
approximately 2.7° C. in the presence of a molar ratio of
14:1 sodium phytate to phytase. As shown in FIGS. 2 and 3,
the melting temperature of phytase increased by approxi-
mately 5.5° C. in the presence of a molar ratio of 130:1
sodium phosphate to phytase. The phosphate does not
appear to be stabilizing background proteins present in the
phytase UFC, which are represented by the first peak of the
chromatogram, but rather is specifically affecting the
phytase enzyme, which is represented by the second peak of
the chromatogram. As shown in FIG. 4, the stabilizing effect
of the sodium phosphate is greater than that of sodium
phytate, sodium polyphosphate, and sodium sulfate at
equivalent molar ratios to the phytase, when normalized for
anion equivalents. Additionally, the mechanism of stabili-
zation does not appear to be a Hofmeister effect. i.e. related
to the extent to which salts act as lyotropes in salting our or
physically stabilizing protein conformation by interacting
with solvating water around the protein, as the increase in
Tm is much higher in the presence of the phosphate rather
than the sulfate, whereas sulfate (see, e.g., Hofmeister F.
(1888) Arch. Exp. Pathol. Pharmacol. 24:247-260; reviewed
in Zhang Y. and Cremer P. S. (2006) Current Opinion in
Chemical Biology. 10:658-63).

Figure 5:
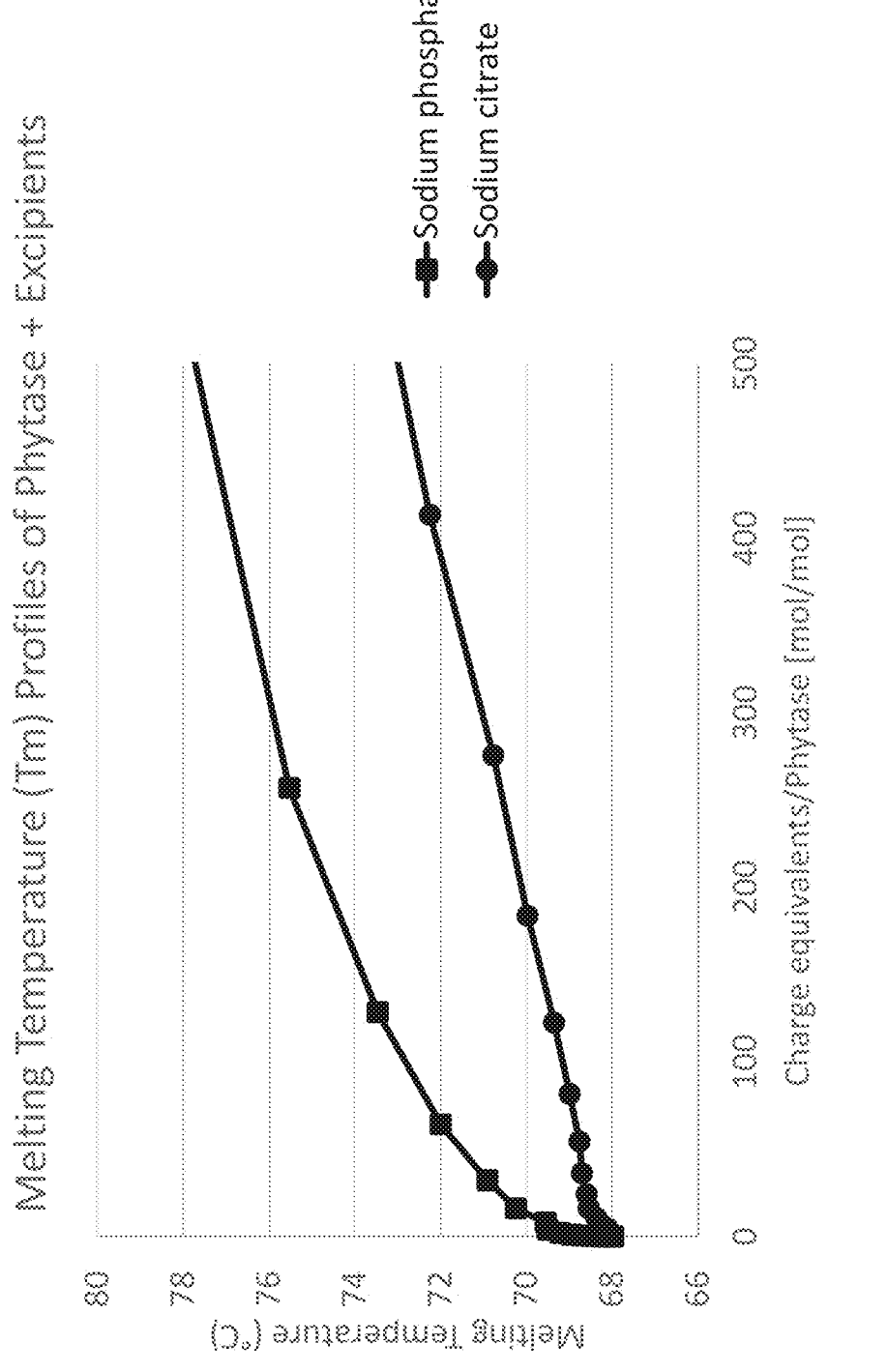
FIG. 5 is a graph showing a comparison of different excipients, normalized in charge equivalents, on the melting temperature of phytase in the liquid state.

As shown in FIG. 5, the mechanism of stabilization also
does not appear to be a charge effect, as the increase in
melting temperature is much higher in the presence of
phosphate rather than citrate when normalized for charge
equivalents.

Example 2: Thermal Inactivation of BP-17 Phytase
in the Presence of Stabilizing Salts An experiment was performed to determine whether the
addition of excipients during thermal stress conditions
allows the phytase enzyme to retain its activity. A tempera-
ture was selected at which the phytase enzyme is completely
inactivated in the absence of excipient after 30-minutes
incubation. Excipient solutions were prepared at their high-
est solubility. then titrated from highest to lowest concen-
trations prior to their addition to the phytase UFC. The
enzyme/excipient combinations were then exposed to a
temperature of 70° C., and the residual activity was mea-
sured after 2, 5, 10, 20, 30, and 60-minutes incubation via a
colorimetric activity assay Materials The following equipment and reagents were used:

BP-17 phytase UFC (70,000 FTU/g or 123.4 g/L phytase)

BP-17 phytase standard (22,000 FTU/g)

BP-17 phytase control (36,500 FTU/g)

0.2 mL PCR strip tubes with 12 wells (VWR 53509-306)

Autoclaved water

Temperature cycler with temperature gradient capabilities 96-well PCR prep racks Large benchtop centrifuge Sodium phosphate dibasic anhydrous (Sigma Aldrich), 141.96 g/mol Sodium citrate dihydrate (J. T. Baker), 294.1 g/mol Phosphoric acid and citric acid for pH adjustment pH meter Assay buffer: 0.1 M acetate buffer pH 5.5 with 0.05% (w/v) Tween 20

Substrate buffer: 0.1 M acetate buffer pH 5.5

Phytic acid sodium salt hydrate (Sigma Aldrich).

Pi Blue stop solution: POPB-500 (BioAssay Systems US)

Corning® 3641, 96-well clear flat bottom polystyrene nonbinding surface microplate VWR® aluminum foils for 96-well plates iEMS incubator SpectraMax 340 microplate reader (Molecular Devices)

Preparation of Stabilizer Salt Solutions

A 20% (or 1.41 M) sodium phosphate solution was prepared by dissolving 5 grams of sodium phosphate dibasic anhydrous into 25 mL of water. The pH was adjusted to 5.5 using concentrated phosphoric acid. A 25% (or 0.85 M) sodium citrate solution was prepared by dissolving 5 grams of sodium citrate dihydrate into 20 mL of water. The pH was adjusted to 5.5 using 80% citric acid.

Preparation of PCR Strips

A volume of 80 µL of the 20% sodium phosphate stock solution was added to the first well of 8 different 12-well PCR strips. A volume of 40 µL of –Q water was added to wells 2, 3. 4, 5, and 6 of each PCR strip. The sodium phosphate stock solution was serially diluted 2-fold sequentially from well 1 to well 6. A volume of 80 µL of the 25% sodium citrate stock solution was added to well 7 of each PCR strip. A volume of 40 µL of water was added to wells 8, 9, 10, 11, and 12 of each PCR strip. The sodium citrate stock solution was serially diluted 2-fold sequentially from well 7 to well 11, leaving well 12 to contain water only. The BP-17 phytase UFC was diluted 50-fold in autoclaved water. A volume of 40 µL of the diluted UFC was added to each well of the 8 different 12-well PCR strips containing the diluted excipients.

Thermal Inactivation

The temperature cycler was programmed to a temperature of 70° C. One PCR strip was sealed and placed immediately on ice for the time zero measurement. The remaining PCR strips were sealed, placed inside the PCR, incubated for varying increments of time (0.5, 2, 5, 10, 20, 30, and 60 minutes), then removed from the PCR and placed immediately on ice. After each of the PCR strips had been collected on ice, they were placed on a 96-well PCR tube rack and centrifuged for 2 minutes at 3500 rpm.

Phytase Activity Assay

As some precipitation occurred during thermal inactivation, the PCR strips were subjected to centrifugation and the supernatant was removed and diluted with assay buffer (0.1 M acetate Buffer pH 5.5+0.05% w/v Tween 20) to a final activity of 0.012 FTU/mL in a non-binding (Corning 3641) 96-well plate. A volume of 40 µL was transferred from the enzyme dilution plate into a separate reaction plate (Costar 9017, medium binding). A volume of 40 µL of substrate (150 µM sodium phytate) was then added to each of the wells of the reaction plate. The reaction plate was sealed and incubated for 10 minutes at 25° C. and 900 rpm. A volume of 170 µL of Pi Blue stop/color reagent (POPB-500 by BioAssay Systems US) was then added to each well of the reaction plate to stop the reaction. The plate was sealed and incubated for 30 minutes at 25° C. and 400 rpm for color development, then read in a spectrophotometer at 620 nm.

Figure 6:
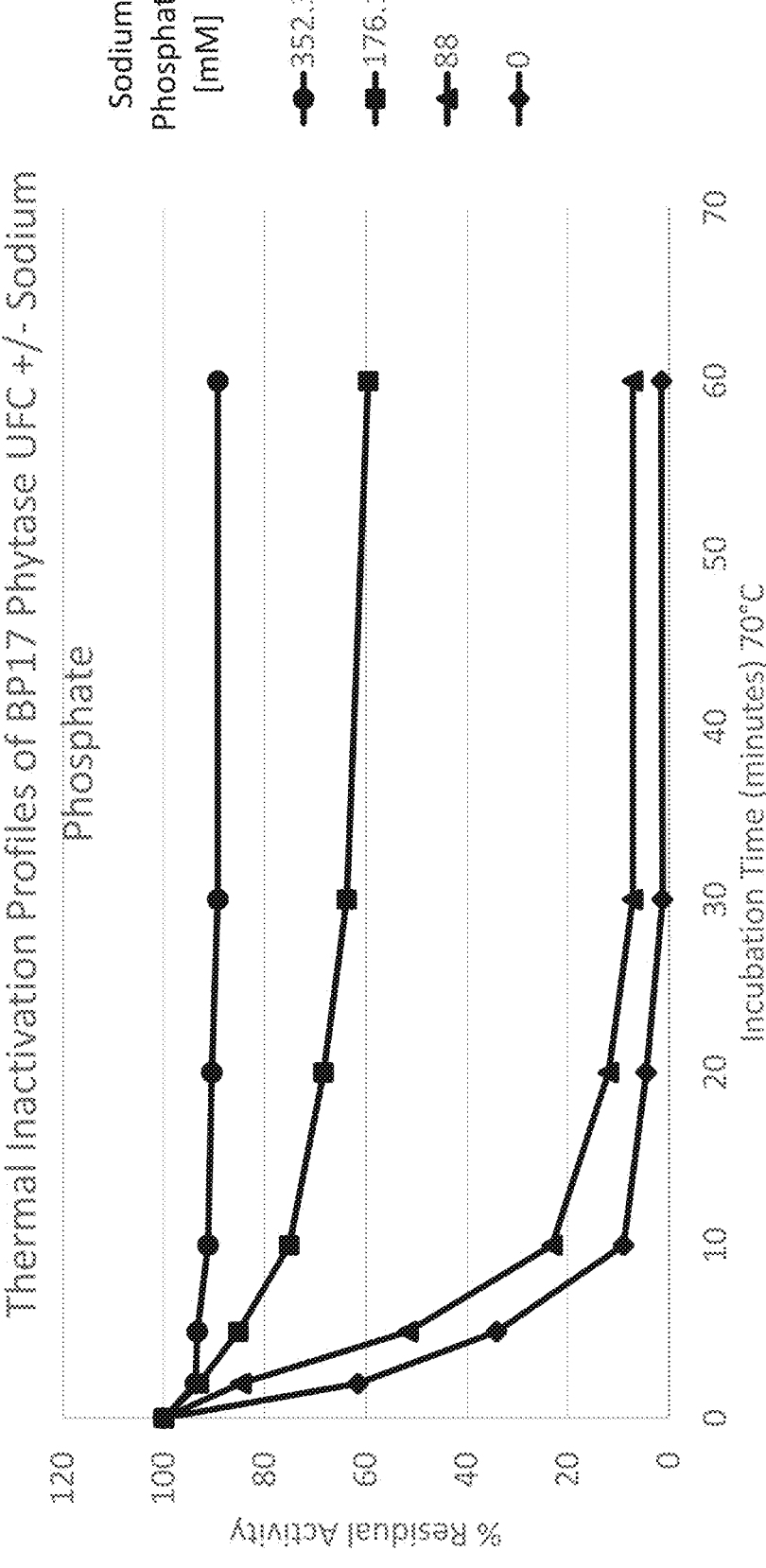
FIG. 6 is a graph showing the thermal inactivation profiles of the phytase UFC with increasing levels of sodium phosphate.
Figure 7:
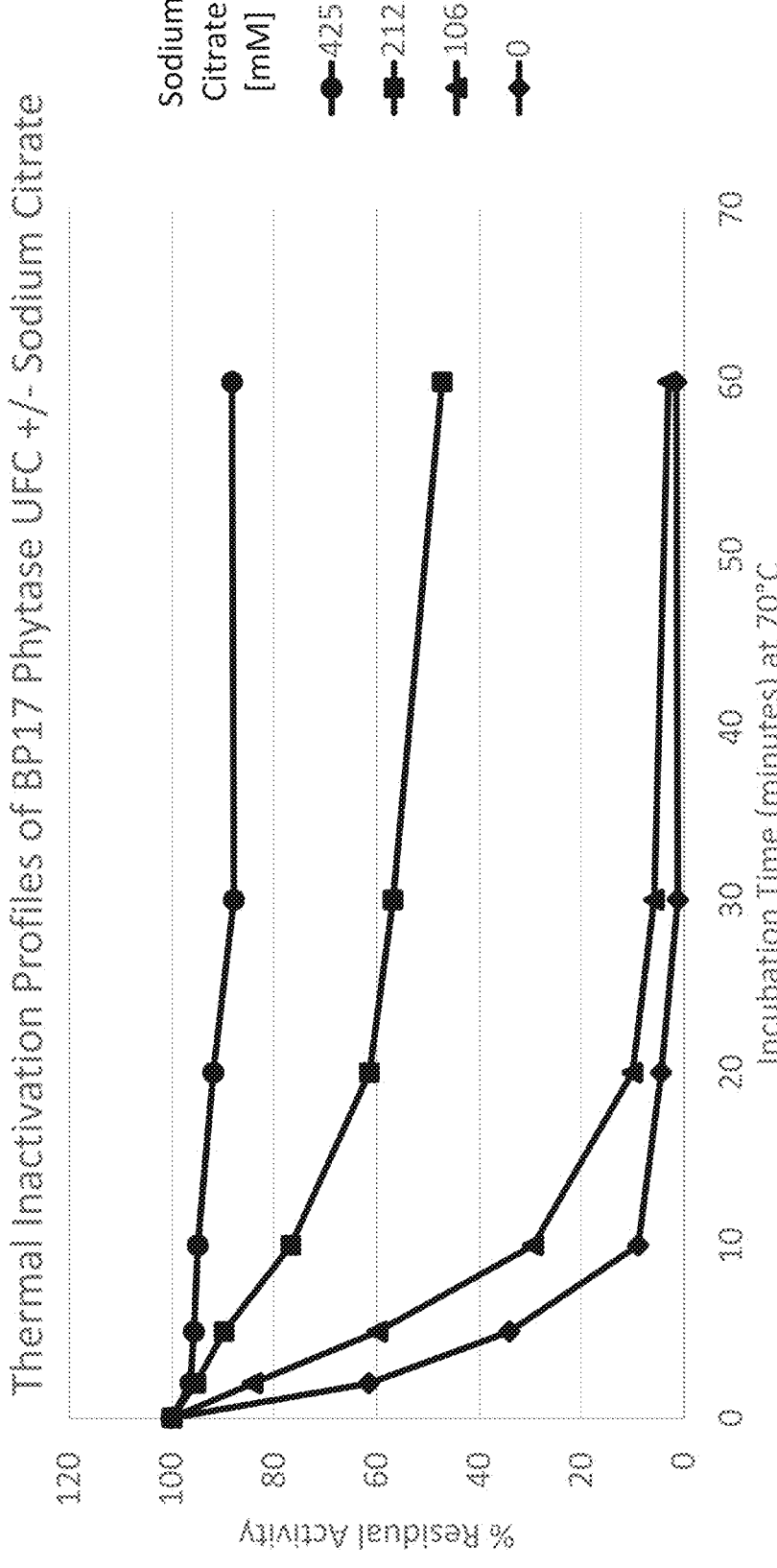
FIG. 7 is a graph showing the thermal inactivation profiles of the phytase UFC with increasing levels of sodium citrate.

As shown in FIG. 6, approximately 90% relative residual phytase activity (as calculated using the % recovered activity described herein) is retained after 60-minutes incubation in the presence of 352 mM sodium phosphate. In the presence of half of that concentration, approximately 60% phytase activity is retained after 60-minutes incubation. Below this concentration, the phytase enzyme appears to be nearly inactivated. As shown in FIG. 7, approximately 90% phytase activity is retained after 60-minutes incubation in the presence of 425 mM sodium citrate. In the presence of half of that concentration, approximately 50% or less phytase activity is retained after 60-minutes incubation. Below this concentration, the phytase enzyme appears to be inactivated. In order to achieve similar activity profiles during thermal stress conditions, a higher concentration of sodium citrate is required compared to sodium phosphate. In this regard, sodium phosphate appears to be a better stabilizer to the phytase than sodium citrate.

Example 3. Mechanism of Inhibition

Kinetic analysis was performed to determine the mechanism of stabilization of both the sodium phosphate and sodium citrate with respect to the phytase enzyme by measuring the activity of phytase in the presence of both titrated substrate and titrated excipient concentrations.

Materials

The following equipment and reagents were used:

BP-17 phytase UFC (70.000 FTU/g or 123.4 g/L phytase)

Sodium phosphate dibasic anhydrous (Sigma Aldrich), 141.96 g/mol

Sodium citrate dihydrate (J. T. Baker), 294.1 g/mol

Phosphoric acid and citric acid for pH adjustment pH meter

Dilution buffer: 0.1 M acetate Buffer pH 5.5 with 0.05% (w/v) Tween 20

4-Nitrophenyl phosphate di (tris) salt (Sigma Aldrich)

Substrate buffer: 0.25 M acetate Buffer pH 5.5

Stop Buffer: 200 mM Borate pH 10.2

Corning 3641, 96-well clear flat bottom polystyrene non-binding surface microplate VWR Aluminum Foils for 96-well plates Eppendorf Thermomixer™ R with microplate block (Fisher Scientific)

SpectraMax 340 Microplate Reader (Molecular Devices)

Preparation of Enzyme and Substrate

The BP-17 phytase UFC was diluted 7,000-fold in 0.1 M acetate buffer pH 5.5.

The substrate stock solution (400 mM) was prepared by dissolving 0.923 grams of 4-nitrophenyl phosphate di (tris) salt into 5 mL of 0.25 M acetate buffer pH 5.5. A volume of 200 µL of the substrate stock solution was added to columns 1 and 7 of a 96-well plate. A volume of 100 µL of 0.25 M acetate Buffer pH 5.5 was added to columns 2-6 and 8-12 of the same 96-well plate. Serial dilutions were performed by transferring 100 µL from column 1 into column 2 of the 96-well plate, and then repeating this dilution pattern across the plate to column 6 so that the following substrate concentrations were made: 400, 200, 100, 50, 25, and 12.5 mM. The same serial dilutions were performed across the second half of the plate from columns 7 to 12.

Preparation of Sodium Phosphate

A 20% (or 1.41 M) sodium phosphate solution was prepared by dissolving 5 grams of sodium phosphate dibasic anhydrous into 25 mL of 0.1 M acetate buffer pH 5.5. The 20% sodium phosphate solution was then diluted 7-fold by combining 1 mL of the stock solution with 6 mL of 0.1 M acetate buffer pH 5.5, making a concentration of 200 mM. A volume of 200 μL of the sodium phosphate solution (200 mM) was added to each well in row A of a 96-well plate. A volume of 100 μL of the 0.1 M acetate buffer pH 5.5 was added to each well in rows B-H of the same 96-well plate. Serial dilutions (2-fold) were performed by transferring 100 μL from row A into row B of the 96-well plate, and then repeating this dilution pattern down the plate to row G so that the following sodium phosphate concentrations were created: 200, 100, 50, 25, 12.5, 6.25, 3.125, and 0 mM.

Preparation of Sodium Citrate

A 25% (or 0.85 M) sodium citrate solution was prepared by dissolving 5 grams of sodium citrate dihydrate into 20 mL of 0.1 M acetate buffer pH 5.5. A volume of 200 μL of the sodium citrate solution (0.85 M) was added to each well in row A of a new 96-well plate. A volume of 100 μL of the 0.1 M acetate buffer pH 5.5 was added to each well in rows B-H of the same 96-well plate. Serial dilutions (2-fold) were performed by transferring 100 μL from row A into row B of the 96-well plate, and then repeating this dilution pattern down the plate to row G so that the following sodium citrate concentrations were created: 850, 425, 212.5, 106.25, 53.13, 26.56, 13.28, and 0 mM.

Preparation of Substrate/Excipient Plate

Two identical 96-well substrate plates were prepared by adding 25 μL of the titrated substrate concentrations to columns 1-6 and to columns 7-12 of both plates. A volume of 75 μL of the titrated sodium phosphate concentrations was transferred to each corresponding well of the first substrate plate to make the following concentrations of substrate and excipient:

100, 50, 25, 12.5, 6.25, and 3.125 mM substrate
150, 75, 37.5, 18.75, 9.38, 4.69, and 2.34 mM sodium phosphate A volume of 75 μL of the titrated sodium citrate concentrations was transferred to each corresponding well of the second substrate plate to make the following concentrations of substrate and excipient:

100, 50, 25, 12.5, 6.25, and 3.125 mM substrate
637.5, 425, 212.5, 106.25, 53.13, 26.56, and 13.28 mM sodium citrate PNPP Assay A volume of 5 μL of the 7,000-fold diluted BP-17 phytase UFC was added to columns 1-6 of an empty 96-well plate. A volume of 5 μL of the 0.1 M acetate buffer pH 5.5 was added to columns 7-12 of the same 96-well plate to serve as the blanks. An identical plate was set up in the same manner. A volume of 55 μL of the substrate/phosphate combinations was added to each corresponding well of the first 96-well plate containing the diluted UFC. A volume of 55 μL of the substrate/citrate combinations was added to each corresponding well of the second 96-well plate containing the diluted UFC. The two 96-well reaction plates were sealed and placed in thermomixers at 25° C., 650 rpm for 15 minutes. Upon completion of the reaction, a volume of 70 μL of the Borate Stop buffer (200 mM) pH 10.2 was added to each well. The plates were sealed and placed on plate shaker for 1 minute at 25° C. and 650 rpm, then read in a spectrophotometer at 405 nm. The PNPP assay measures the dephoshorylation of p-nitrophenyl phosphate to p-nitrophenol, which becomes a yellow soluble product that can be measured on a spectrophotometer at a wavelength of 405 nm.

Figure 8:
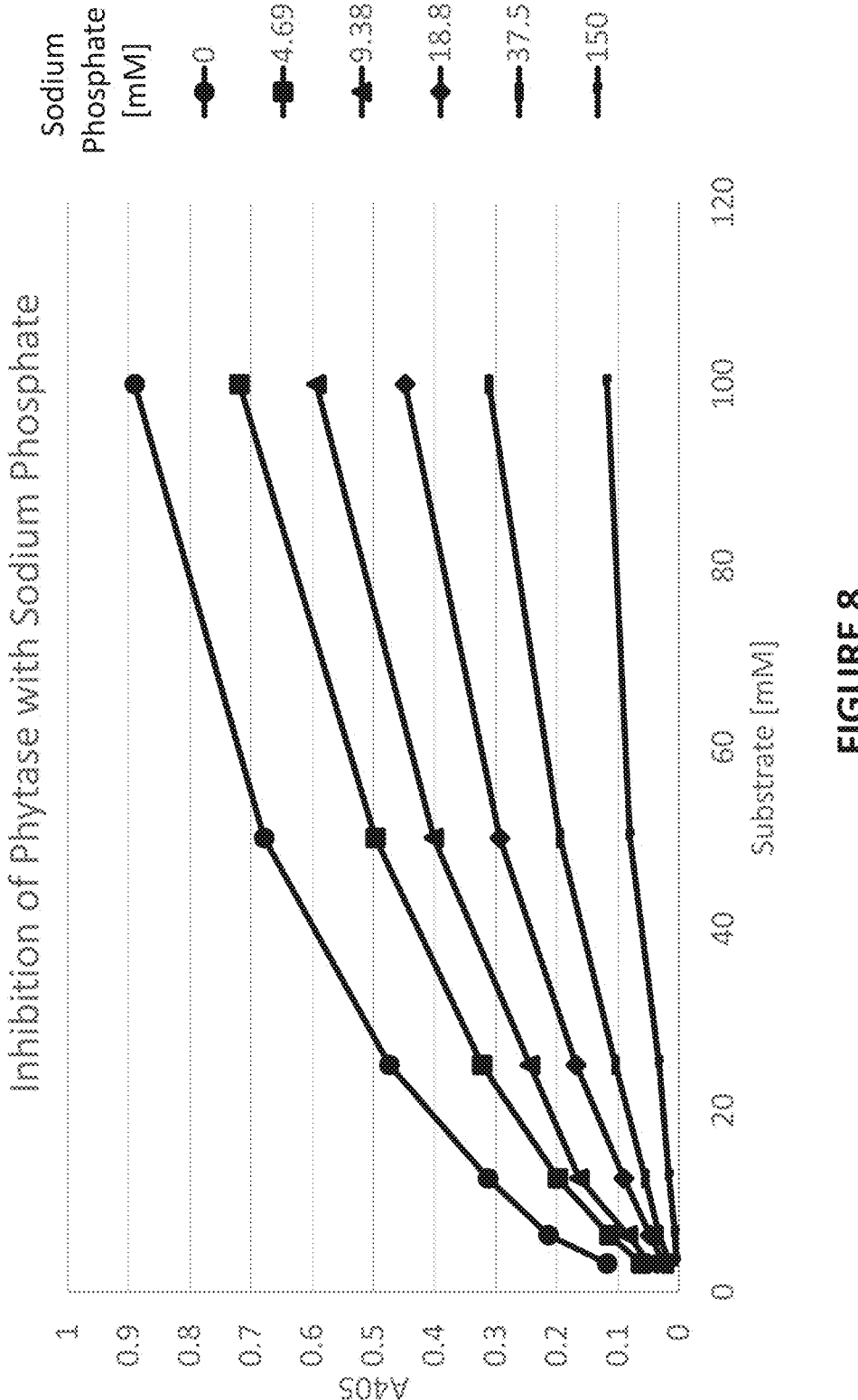
FIG. 8 is a graph showing competitive inhibition of phytase in the presence of phytic acid substrate and increasing levels of sodium phosphate.
Figure 9:
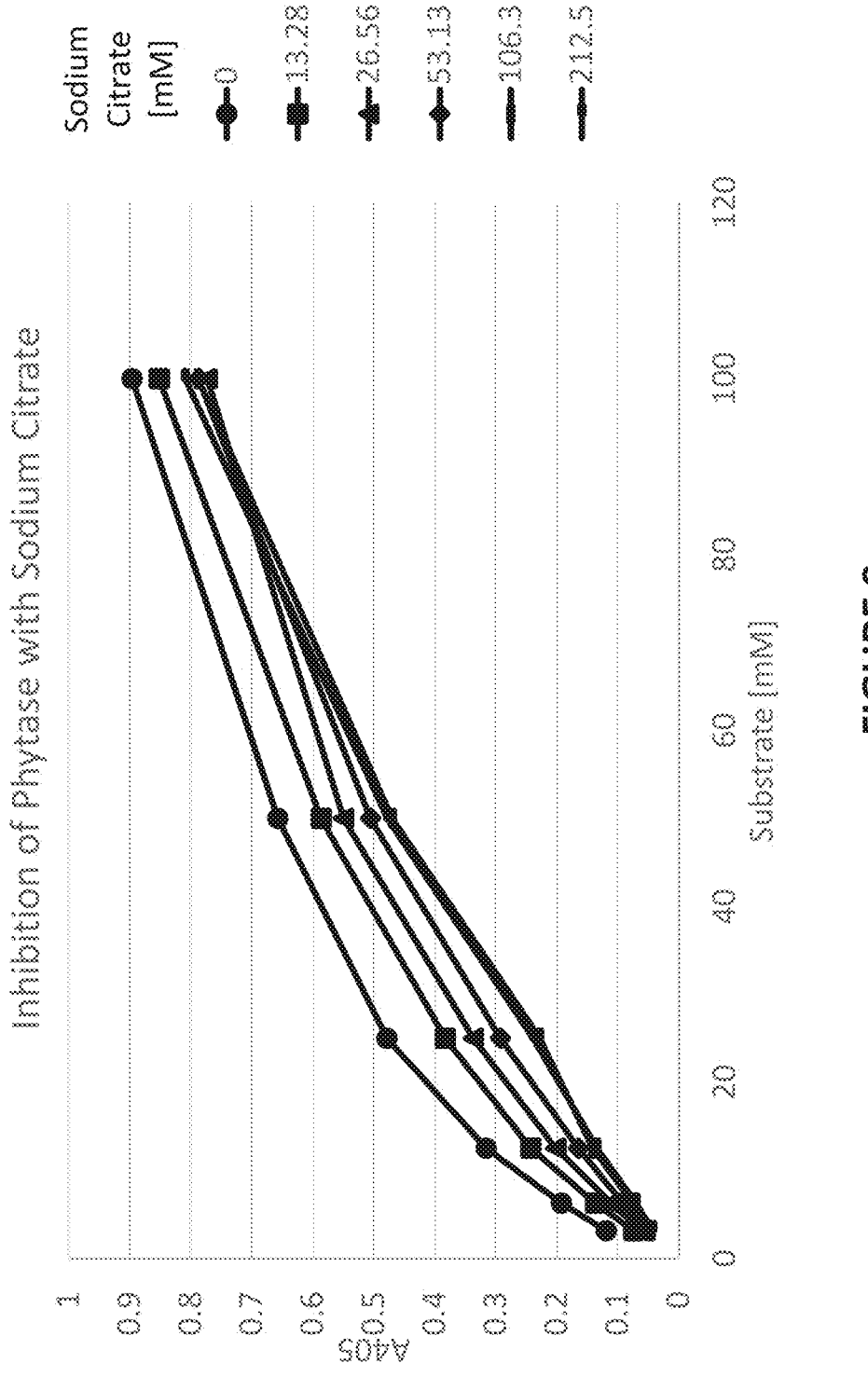
FIG. 9 is a graph showing competitive inhibition of phytase in the presence of phytic acid substrate and increasing levels of sodium citrate.

As shown in FIG. 8, increasing concentrations of sodium phosphate reduced the activity of the phytase enzyme in the presence of increasing concentrations of phytic acid substrate under ambient assay conditions. At a concentration of 150 mM sodium phosphate and 100 mM phytic acid substrate, the phytase enzyme shows very little activity. Sodium phosphate inhibits the activity of the enzyme in the presence of phytic acid substrate; therefore, it must compete for the active site of the enzyme. As shown in FIG. 9, low concentrations of sodium citrate begin to reduce the activity of the phytase enzyme in the presence of increasing concentrations of phytic acid substrate under ambient assay conditions, but the activity loss appears to level out at concentrations of 26 mM or higher. Accordingly, the mechanism of stabilization for sodium citrate must be different from that of sodium phosphate on the phytase enzyme.

Example 4. Granulation and Pelleting Performance

Multi-layered enzyme granules were produced using a fluid-bed spray process as described in U.S. Pat. No. 5,324, 649 (see also U.S. Pat. Pub. No. 2015037491), which are incorporated by reference. Granules were prepared with (A) no recipient, (B) phytate or (C) phosphate as summarized in Table 1.

TABLE 1

| Composition of granules | | | | | |
|---|---|---|---|---|---|
| Granule | Stabilizer | Percent stabilizer in granule (% w/w) | Percent stabilizer in phytase layer (% w/w) | Molarity stabilizer in phytase layer (mM) | Effective phosphate: phytase molar ratio |
| A | None | 0.0 | 0.0 | 0 | 0 |
| B | Sodium phytate | 0.5 | 3.6 | 9 | 26 |
| C | Sodium phosphate | 1.9 | 12.2 | 250 | 122 |

Prior to pelleting, the granules were compared for recovered activity using a steam simulator device steam process simulator, which applicants have found to be predictive for pelleting stability. The steam process simulator consists of a source of saturated steam plumbed to a flexible hose, approximately ¼" in internal diameter plumbed into a 3-way valve that feeds a receiving chamber about 6" in diameter, on top of which can be placed a sieve screen of matching diameter. The 3-way valve is also plumbed to a vacuum line, such that entry steam feed can be instantaneously switched off at the same time the vacuum line is activated.

Figure 10:
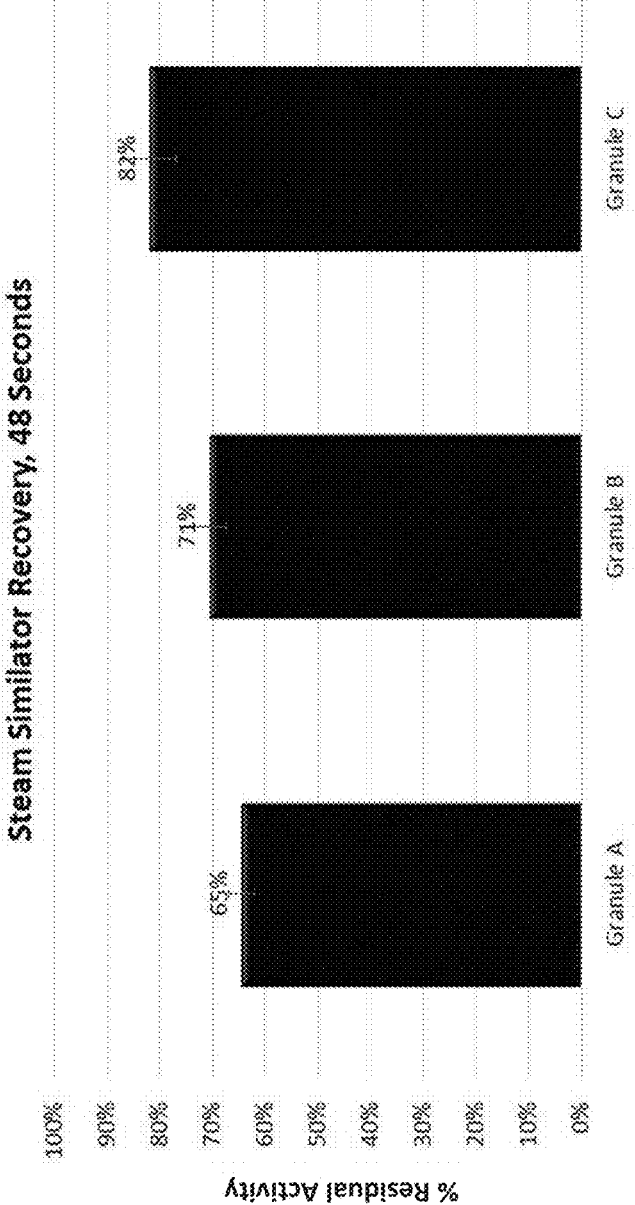
FIG. 10 is a graph showing steam simulator recovery of granules having (A) no recipient, (B) phytate or (C) phosphate.

To run the steam process simulator test, approximately 1-2 grams of phytase enzyme granules were placed on the sieve screen. The steam feed line was opened such that steam flowed slowly up through the screen and contacted the enzyme granules for a defined number of seconds, after which the 3-way valve is turned to shut off feed and induce reverse flow of ambient air back across the granules, thereby instantly halting contact with steam and inducing rapid cooling and drying. The sieve screen and steam granules were removed from the steam process simulator and allowed to air dry overnight. The granules were then assayed for retained phytase activity, and the phytase activity recovery is calculated for the retained phytase activity as a percentage of the phytase activity of the initial unsteamed granules prior to steaming. FIG. 10 shows the percent of phytase activity recovered in granules subjected to 48-seconds of simulated steam treatment, compared to granules that were not subjected to simulated streaming. Stabilization with phosphate provided 11% better recovery than stabilization with phytate.

The granules were combined with a mixture of 60% corn meal and 40% soy meal (i.e. the mash) at a ratio of 60 grams of granules to 120 kilograms of corn-soy meal such that the final activity of phytase in the mixture before pelleting was approximately 5 units/gram.

This mixture was then pelleted in an animal feed pelleter. The granules and the corn-soy meal were blended in a horizontal ribbon mixer, for approximately 8 minutes. The pellet mill was a Simon Heesen, mono roll type, fitted with a 17.3 cm inner diameter die, with a pellet hole diameter of 3 mm. Die speed was 500 rpm and was driven by a 7.5 KW motor. The typical feed rate was 300 kg per hour. The temperature in the conditioner was kept at +/−0.1° C., measured at the feed outlet from the conditioner. The conditioner had a cascade type mixer system. The conditioning temperatures was 100° C. Steam inlet pressure was 2 atm, and the temperature in the conditioner was controlled by manual adjustment of three valves that regulate the steam delivery. The residence time in the conditioner 30 or 60 seconds. When the target temperature was reached, the system was run for approximately 5 to 10 minutes before sampling took place. Samples were taken for 1-1.5 minute periods, corresponding to 5-7.5 kg of pelleted feed, and were immediately placed in a cooling box with a perforated bottom and air flow of 1500 cubic meters per hour. After cooling for 15 minutes, the samples were downsized 5 times using a sample divider, and 250 g was taken for lab tests. After pelleting and cooling, the pellets were then ground up and assayed for phytase activity.

Figure 11:
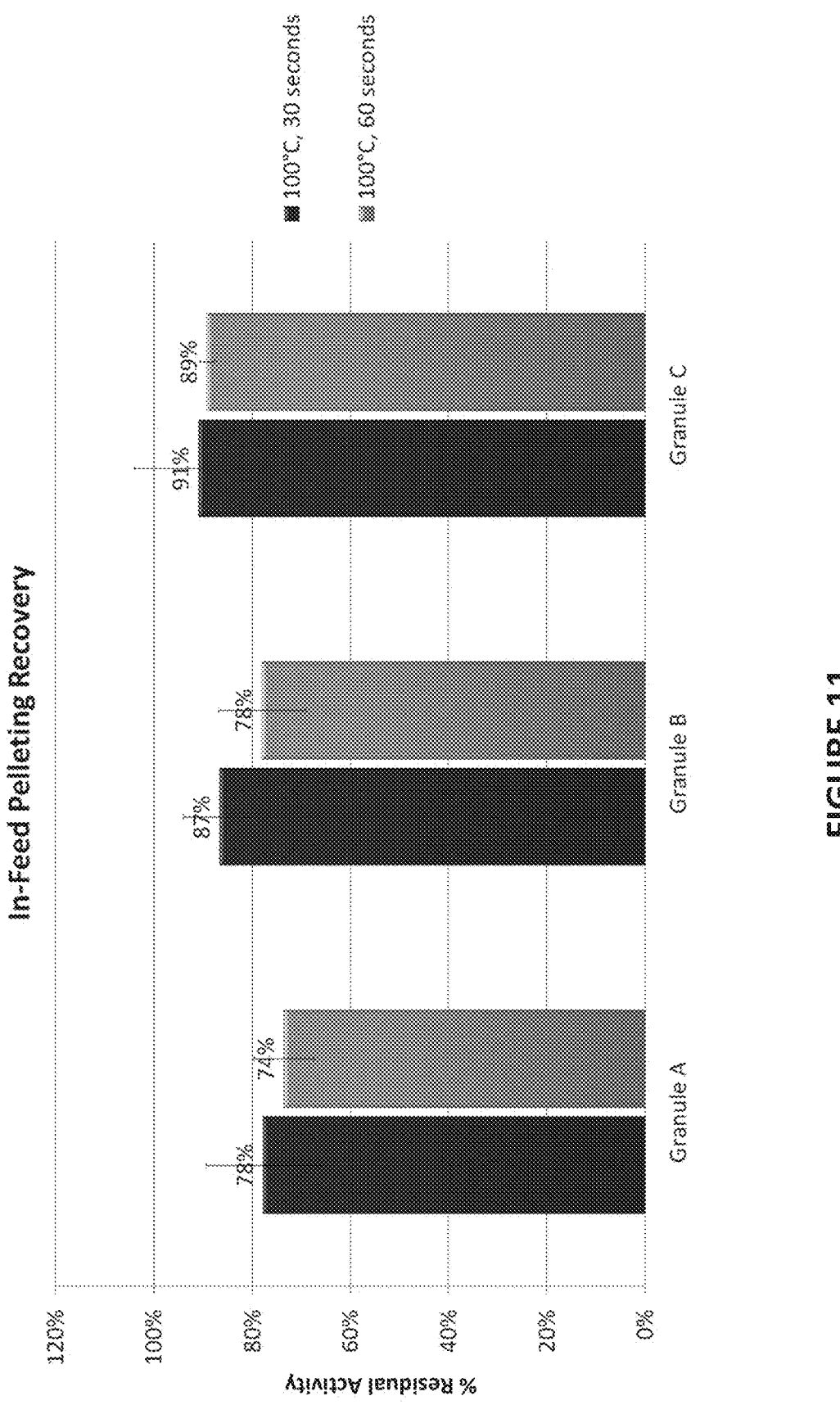
FIG. 11 is a graph showing in-feed pelleting recovery of granules having (A) no recipient, (B) phytate or (C) phosphate.

The percent of phytase activity recovered in granules pelleted at 100° C. for 30 or 60 seconds, compared to the phytase activity in non-pelleted granules, using the % recovered activity formula provided herein, is shown in FIG. 11. Stabilization with phosphate provided 4% better recovery than stabilization with phytate after 30 seconds and 11% better recovery after 60 seconds.

Although the foregoing compositions and methods have been described in detail by way of illustration and examples for purposes of clarity and understanding, it will be apparent that certain changes and modifications may be practiced without departing from the spirit and scope of the present compositions and methods. Accordingly, the description should not be construed as limiting the scope of the present compositions and methods that are delineated by the appended claims. All publications, patents, and patent applications cited herein are hereby incorporated by reference in their entireties for all purposes

---

What is claimed is:

1. A granule composition comprising phosphate and phytase, wherein the granule is a multi-layered granule, wherein the phosphate and phytase are in functional proximity and at a molar ratio of at least 50:1 and wherein the phosphate is not a hydrolysis product of phytate, wherein the phosphate comprises sodium phosphate or potassium phosphate and the phosphate and phytase are incorporated into a single layer of the multi-layered granule.

2. The granule of claim 1, wherein the granule is a matrix granule.

3. The granule of claim 1, wherein the phytase and phosphate are incorporated into the core of the granule.

4. The granule of claim 1, wherein the granule does not contain phytate.

5. The granule of claim 1, wherein the phosphate is a monophosphate.

6. The granule of claim 1, wherein the DSC Tm of the phytase is increased by at least 2.7° C. compared to a control phytase not stabilized by phosphate at a concentration molar ratio of phosphate to phytase of at least 50:1.

* * * * *

SEQUENCE LISTING

```
<160> NUMBER OF SEQ ID NOS: 4

<210> SEQ ID NO 1
<211> LENGTH: 413
<212> TYPE: PRT
<213> ORGANISM: Buttiauxella sp.

<400> SEQUENCE: 1

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175
```

-continued

```
Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
            195                 200                 205

Ala Leu Asp Gly Ala Ile Gly Leu Ser Ser Thr Leu Ala Glu Ile Phe
            210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
            290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
            370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

```
<210> SEQ ID NO 2
<211> LENGTH: 413
<212> TYPE: PRT
<213> ORGANISM: Buttiauxella sp.

<400> SEQUENCE: 2

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
```

-continued

```
          130                135                140

Ala Val Glu Lys Glu Ala Gln Thr Pro Ile Asp Asn Leu Asn Gln His
145                150                155                160

Tyr Ile Pro Ser Leu Ala Leu Met Asn Thr Thr Leu Asn Phe Ser Lys
              165                170                175

Ser Pro Trp Cys Gln Lys His Ser Ala Asp Lys Ser Cys Asp Leu Gly
          180                185                190

Leu Ser Met Pro Ser Lys Leu Ser Ile Lys Asp Asn Gly Asn Glu Val
          195                200                205

Ser Leu Asp Gly Ala Ile Gly Leu Ser Ser Thr Leu Ala Glu Ile Phe
      210                215                220

Leu Leu Glu Tyr Ala Gln Gly Met Pro Gln Ala Ala Trp Gly Asn Ile
225                230                235                240

His Ser Glu Gln Glu Trp Ala Leu Leu Leu Lys Leu His Asn Val Tyr
              245                250                255

Phe Asp Leu Met Glu Arg Thr Pro Tyr Ile Ala Arg His Lys Gly Thr
          260                265                270

Pro Leu Leu Gln Ala Ile Ser Asn Ala Leu Asn Pro Asn Ala Thr Glu
          275                280                285

Ser Lys Leu Pro Asp Ile Ser Pro Asp Asn Lys Ile Leu Phe Ile Ala
      290                295                300

Gly His Asp Thr Asn Ile Ala Asn Ile Ala Gly Met Leu Asn Met Arg
305                310                315                320

Trp Thr Leu Pro Gly Gln Pro Asp Asn Thr Pro Pro Gly Gly Ala Leu
              325                330                335

Val Phe Glu Arg Leu Ala Asp Lys Ser Gly Lys Gln Tyr Val Ser Val
              340                345                350

Ser Met Val Tyr Gln Thr Leu Glu Gln Leu Arg Ser Gln Thr Pro Leu
          355                360                365

Ser Leu Asn Gln Pro Ala Gly Ser Val Gln Leu Lys Ile Pro Gly Cys
      370                375                380

Asn Asp Gln Thr Ala Glu Gly Tyr Cys Pro Leu Ser Thr Phe Thr Arg
385                390                395                400

Val Val Ser Gln Ser Val Glu Pro Gly Cys Gln Leu Gln
              405                410
```

```
<210> SEQ ID NO 3
<211> LENGTH: 413
<212> TYPE: PRT
<213> ORGANISM: Buttiauxella sp.

<400> SEQUENCE: 3

Asn Asp Thr Pro Ala Ser Gly Tyr Gln Val Glu Lys Val Val Ile Leu
1               5                10                15

Ser Arg His Gly Val Arg Ala Pro Thr Lys Met Thr Gln Thr Met Arg
              20                25                30

Asp Val Thr Pro Asn Thr Trp Pro Glu Trp Pro Val Lys Leu Gly Tyr
          35                40                45

Ile Thr Pro Arg Gly Glu His Leu Ile Ser Leu Met Gly Gly Phe Tyr
      50                55                60

Arg Gln Lys Phe Gln Gln Gln Gly Ile Leu Ser Gln Gly Ser Cys Pro
65                70                75                80

Thr Pro Asn Ser Ile Tyr Val Trp Thr Asp Val Ala Gln Arg Thr Leu
              85                90                95
```

-continued

```
Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
        130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
            195                 200                 205

Ser Leu Asp Gly Ala Ile Gly Leu Ser Ser Thr Leu Ala Glu Ile Phe
        210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
            325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
        370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

```
<210> SEQ ID NO 4
<211> LENGTH: 413
<212> TYPE: PRT
<213> ORGANISM: Buttiauxella sp.

<400> SEQUENCE: 4
```

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
        50                  55                  60
```

```
Arg Gln Lys Phe Gln Gln Gln Gly Ile Leu Pro Arg Gly Ser Cys Pro
65              70              75              80

Thr Pro Asn Ser Ile Tyr Val Trp Thr Asp Val Ala Gln Arg Thr Leu
            85              90              95

Lys Thr Gly Glu Ala Phe Leu Ala Gly Leu Ala Pro Gln Cys Gly Leu
            100             105             110

Thr Ile His His Gln Gln Asn Leu Glu Lys Ala Asp Pro Leu Phe His
            115             120             125

Pro Val Lys Ala Gly Ile Cys Ser Met Asp Lys Thr Gln Val Gln Gln
        130             135             140

Ala Val Glu Lys Glu Ala Gln Thr Pro Ile Asp Asn Leu Asn Gln Arg
145             150             155             160

Tyr Ile Pro Glu Leu Ala Leu Met Asn Thr Ile Leu Asn Phe Ser Lys
            165             170             175

Ser Pro Trp Cys Gln Lys His Ser Ala Asp Lys Pro Cys Asp Leu Ala
            180             185             190

Leu Ser Met Pro Ser Lys Leu Ser Ile Lys Asp Asn Gly Asn Glu Val
        195             200             205

Ser Leu Asp Gly Ala Ile Gly Leu Ser Ser Thr Leu Ala Glu Ile Phe
    210             215             220

Leu Leu Glu Tyr Ala Gln Gly Met Pro Gln Val Ala Trp Gly Asn Ile
225             230             235             240

His Ser Glu Gln Glu Trp Ala Leu Leu Leu Lys Leu His Asn Val Tyr
            245             250             255

Phe Asp Leu Met Glu Arg Thr Pro Tyr Ile Ala Arg His Lys Gly Thr
            260             265             270

Pro Leu Leu Gln Ala Ile Ser Asn Ala Leu Asn Pro Asn Ala Thr Glu
            275             280             285

Ser Lys Leu Pro Asp Ile Ser Pro Asp Asn Lys Ile Leu Phe Ile Ala
    290             295             300

Gly His Asp Thr Asn Ile Ala Asn Ile Ala Gly Met Leu Asn Met Arg
305             310             315             320

Trp Thr Leu Pro Gly Gln Pro Asp Asn Thr Pro Pro Gly Gly Ala Leu
            325             330             335

Val Phe Glu Arg Leu Ala Asp Lys Ser Gly Lys Gln Tyr Val Ser Val
            340             345             350

Ser Met Val Tyr Gln Thr Leu Glu Gln Leu Arg Ser Gln Thr Pro Leu
            355             360             365

Ser Leu Asn Gln Pro Pro Gly Ser Val Gln Leu Lys Ile Pro Gly Cys
    370             375             380

Asn Asp Gln Thr Ala Glu Gly Tyr Cys Pro Leu Ser Thr Phe Thr Arg
385             390             395             400

Val Val Ser Gln Ser Val Glu Pro Gly Cys Gln Leu Gln
            405             410
```